US 7,226,772 B2

United States Patent
Hseu et al.

(10) Patent No.: US 7,226,772 B2
(45) Date of Patent: Jun. 5, 2007

(54) RECOMBINANT XYLANASES DERIVED FROM ANAEROBIC FUNGI, AND THE RELEVANT SEQUENCES, EXPRESSION VECTORS AND HOSTS

(75) Inventors: Ruey-Shyang Hseu, Taipei (TW); Ya-Hui Huang, Hsinchu (TW)

(73) Assignee: Geneway Biotechnology Corporation, Banchiau (TW)

(*) Notice: Subject to any disclaimer, the term of this patent is extended or adjusted under 35 U.S.C. 154(b) by 471 days.

(21) Appl. No.: 10/244,596

(22) Filed: Sep. 17, 2002

(65) Prior Publication Data
US 2004/0053238 A1 Mar. 18, 2004

(51) Int. Cl.
C12N 9/24 (2006.01)
C12N 1/20 (2006.01)
C07H 21/04 (2006.01)

(52) U.S. Cl. ............... 435/200; 435/4; 435/6; 435/69.1; 435/183; 435/252.3; 435/320.1; 536/23.2; 536/23.4; 536/23.5; 536/23.7

(58) Field of Classification Search ............... 435/4, 435/6, 69.1, 183, 193, 200, 209, 210, 252.3, 435/252.8, 254.1, 254.23, 320.1; 536/23.2, 536/23.4, 23.7, 23.74
See application file for complete search history.

(56) References Cited

U.S. PATENT DOCUMENTS 5,824,533 A 10/1998 Li et al.
5,948,667 A 9/1999 Cheng et al.
6,300,114 B1 10/2001 Mäntylä et al.

FOREIGN PATENT DOCUMENTS

WO 93/25693 12/1993

OTHER PUBLICATIONS

Gilbert et al. (GenBank Accession No. A75565, Oct. 15, 1999).*
Xue GP (GenBank Accession No. AX033851, Sep. 21, 2000).*
Gilbert et al. (GenBank Accession No. X65526, May 5, 1992).*
Durand et al. (GenBank Accession No. X82266, Apr. 20, 1997).*
"Current Protocols in Molecular Biology: vol. 1"; pp. 1.8.1-1.8.3 (1994).
Ronald M. Teather et al., "Use of Congo Red-Polysaccharide Interactions in Enumeration and Characterization of Cellulolytic Bacteria from the Bovine Rumen", *Applied and Environmental Microbiology*, vol. 43, No. 4, pp. 777-780 (1983).
Gail Lorenz Miller, "Use of Dinitrosalicylic Acid Reagent for Determination of Reducing Sugar", *Analytical Chemistry*, vol. 31, No. 3, pp. 426-428 (1959).
Jacques Georis et al., "Sequence, Overproduction and Purification of the Family 11 endo-β-1,4-xylanase Encoded by the *xyl1* gene of *Streptomyces* sp. S38", *Gene*, vol. 237, pp. 123-133 (1999).
Q.K. Beg et al., "Microbial Xylanases and Their Industrial Applications: A Review", *Appl. Microbiol Biotechnol.*, vol. 56, pp. 326-338 (2001).

(Continued)

Primary Examiner—Manjunath Rao
(74) Attorney, Agent, or Firm—Harness, Dickey & Pierce

(57) ABSTRACT

The present invention provides recombinant xylanases which are derived from anaerobic fungi, particularly *Neocallimastix frontalis* and *N. patriciarum*. The enzymes are thermo- and alkaline pH-tolerable, and highly specific for xylans with high activity.

4 Claims, 12 Drawing Sheets

OTHER PUBLICATIONS

James B. Russell et al., "Factors That Alter Rumen Microbial Ecology", *SCIENCE*, vol. 292, pp. 1119-1122 (2001).

L.B. Selinger et al., "The Rumen: A Unique source of Enzymes of Enhancing Livestock Production", *Anaerobe*, vol. 2, pp. 263-284 (1996).

Roger Durand et al., "Molecular Characterization of *xyn3*, A member of the Endoxylanase Multigene Family of the Rumen Anaerobic Fungus *Neocallimastix Frontalis*", *Curr. Genet*, vol. 30, pp. 531-540 (1996).

Cristina Fanutti et al., "The Conserved Naoncatalytic 40-Residue Sequence in Cellulases and Hemicellulases from Anaerobic Fungi Functions as a Protein Docking Domain", *The Journal of Biological Chemistry*, vol. 270, No. 49, pp. 29314-29322 (1995).

Colin G. Orpin et al., "*Neocallimastix patricuiarum* Sp.Nov., A New Member of the Neocallimasticaceae Inhabiting the Rumen of Sheep", *Trans. Br. Myco. Soc.*, vol. 86, No. 1, pp. 178-180 (1986).

Patrick Kemp et al., "The Lipids of the Rumen Fungus *Piromonas Communis*", *Journal of General Microbiology*, vol. 130, pp. 27-37 (1984).

Jean-Marc Moncalvo et al., "Phylogenetic Relationships in *Ganoderma* Inferred from the Internal transcribe Spacers and 25S Ribosomal DNA Sequences", *Mycologia*, vol. 87, No. 2, pp. 223-238 (1995).

* cited by examiner

```
                        10        20        30        40        50        60        70        80
                   ...|....|....|....|....|....|....|....|....|....|....|....|....|....|....|....|
patent/AAK25847  1  TLAQSFCSS--ASHSGQSVKETG---NKVGTIGGVGYBLWAD--SGHNSATFYSDGSFSCTF---QNAGDYLCRSGLSFD   70
patent/AAK12389  1  .V.KAQUGGNGGASA..RLSVG.GQNQHK.VFD.FS..I.L.NTG.SG.H.LGKGAT.KAEUSAAV.R.NF.A.R..D.G   80
SK1-14           1  .V.KAQUGG..GASA.KLSVG.GQNQHK.VSD.FS..I.L.NTG.SG.HILG.GAT.KAEUNAAV.R.NF.A.R..D.G   78
SK1-11           1  .V.KAQUGG..GASA.KLSVG.GQNQHK.VSD.FS..I.L.NTG.SG.HILG.GAT.KAEUNAAV.R.NF.A.R..D.G   78
SK1-2            1  .V.KAQUGG..GASA.KLSVG.GQNQYK.VSD.FS..I.L.NTG.SG.H.LG.GAT.KAEUNAAV.R.NF.A.R..D.G   78
SK1-12           1  .V.KAQUGG..GASA.KLSVG.GQNQHK.VSD.FS..I.L.NTG.SG.H.LG.GAT.KAEUNAAV.R.NF.A.R..D.G   78
SK1-18           1  .V.KAQUGG..GASA.KLSVG.GQNQHK.VSD.FS..I.L.NTG.SG.H.LG.GAT.KAEUNAAV.R.NF.A.R..D.G   78
SK1-20           1  .V.KAQUGG..GASA.KLSVG.GQNQHK.VSD.FS..I.L.NTG.SG.H.LG.GAT.KAEUNAAV.R.NF.A.R..D.G   78
W1-A1            1  .V.KAQUGG..GASA.KLSVG.GQNQHK.VSD.FS..I.L.NTG.SG.H.LG.GAT.KAEUNAAV.R.NF.A.R..D.G   78
W1-A2            1  .V.KAQUGG..GASA.KLSVG.GQNQHK.VSD.FS..I.S.NTG.SG.H.LG.GAT.KAEUNAAV.R.NF.A.R..D.G   78
W1-11            1  .V.KAQUGG..GASA.KLSVG.GQNQHK.VSD.FS..I.L.NTG.SG.HILG.GAT.KAEUNAAV.R.NF.A.R..D.G   78
SK1-15           1  .V.KAQUGG..GACA.KLSVG.GQNQHK.VSD.FS..I.L.NTG.SG.H.LG.GAT.KAEUNAAV.R.NF.A.R..D.G   78
SK1-9            1  .V.KAQUGG..GASA.KLSVG.GQNQHK.VSD.FS..I.L.NTG.SG.H.LG.GAT.KAEUNAAV.R.NF.A.R..D.G   78
W1-4             1  .V.KAQUGG..GASA.KLSVG.GQNQHK.VSD.FS..I.L.NTG.SG.H.LG.GAT.KAEUNAAV.R.NF.A.R..D.G   78

90       100       110       120       130       140       150       160
                   ...|....|....|....|....|....|....|....|....|....|....|....|....|....|....|....|
patent/AAK25847 71  STKTPSQIGRHKADFKLVKTKYFQCULFLCUCLR-UTRSPLUGILHVDNULSPSPPGDUVGNRKHGSFTIDGAQYTVYRN  149
patent/AAK12389 81  ...KATAYEYIGL.YEASYRQTASASGNSRL.VYG.FQNRG.QGVPLVEYYIIKDUV...PDAQGKMV.......KIFQM  160
SK1-14          79  .Q.KATDYSYIGL.YTATYRQTASASGNSRL.VYG.FQNRG.QGVPLVEYYIIKDUV...PDAQGKMV.......KIFQM  158
SK1-11          79  .Q.KATDYSYIGL.YTATYRQTASASGNSRL.VYG.FQNRG.QGVPLVEYYIIKDUV...PDAQGKMV.......KIFQM  158
SK1-2           79  .Q.KATDYSYIGL.YTATYPQTASASGNSRL.VYG.FQNDG.QCVPLVEYYIIKDUV...PDAQGKMV.......KIIQM  158
SK1-12          79  .Q.KATDYSYIGL.YTATYRQTASASGNSRL.VYG.FQNRG.QGVPLVEYYIIKDUV...PDAQGKMV.......KIFQM  158
SK1-18          79  .Q.KATDYSYIGL.YTVTYRQTASASGNSRL.VYG.FQNRG.QGVPLVEYYIIKDUV...PDAQGKMV.......KIFQM  158
SK1-20          79  .Q.KATDYSYIGL.YTATYRQTASASGNSRL.VYG.FQNRG.QGVPLVEYYIIKDUV...PDAQGKMV.......KIFQM  158
W1-A1           79  .Q.KATDYSYIGL.YTATYRQTASASGNSRL.VYG.FQNRG.QGVPLVEYYIIKDUV...PDAQGKMV.......KIFQM  158
W1-A2           79  .Q.KATDYSYIGL.YTATYRQTASASGNSRL.VYG.FQNRG.QGVPLVEYYIIKDUV...PDAQGKMV.......KIFQM  158
W1-11           79  .Q.KATDYSYIGL.YTATYRQTASASGNSRL.VYG.FQNRG.QCVPLVEYYIIKDUV...PDAQGKMV.......KIFQM  158
SK1-15          79  .Q.KAADYSYIGL.YTATYRQTASASGNSRL.VTG.FQNRG.QGVPLVEYYIIKDUV...PDAQGKMV.......KIFQM  158
SK1-9           79  .Q.KATDYSYIGL.YTATYRQTASASGNSRL.VYG.FQNRG.QGVPLVEYYIIKDUV...PDAQGKMV.......KIFQM  158
W1-4            79  .Q.KATDYSYIGL.YTATYRQTASASGNSRL.VYG.FQNRG.QCVPLVEYYIIKDUV...PDAQGKMV.......KIFQM  158

170       180       190       200       210       220       230       240
                   ...|....|....|....|....|....|....|....|....|....|....|....|....|....|....|....|
patent/AAK25847 150 TRTCPSIDG-NTTFKQYFSIRQQARDCGTIDISAHFDQUEKLGHTHGKLHEARVLGEAGNGNGGVSGTADFPYARVYIGD  228
patent/AAK12389 161 DH...T.N.G.E.......V...K.TS.H.TV.D...KA.SNQ.UGI.N.Y.VALHA.GUQS----..V..V.KLD..TTK 236
SK1-14          159 DH...T.N.GSE.......V...K.TS.H.TV.D..KE.A.Q.UGI.N.Y.VALHA.GUQS----..I..VTKLD..TTQ 234
SK1-11          159 DH...T.N.GSE.......V...K.TS.H.TV.D..KE.A.H.UGI.N.Y.VALHA.GUQS----..I..VTKLD..TTQ 234
SK1-2           159 DH...T.N.GGE.......V...K.TS.H.TV.D..KE.A.Q.UGI.N.Y.VALHA.GUQS     ..I..VTKLD..TTQ 234
SK1-12          159 DH...T.N.GSE.......V...K.TS.H.TV.D..KE.A.Q.UGI.N.Y.VALHA.GUQS----..I..VTKLD..TTQ 234
SK1-18          159 DH...T.N.GSE.......V...K.TS.H.TV.D..KE.A.Q.UGI.N.Y.VALHA.GUQS----..I..VTKLD..TTQ 234
SK1-20          159 DH...T.N.GSE.......V..K.TS.H.TV.D..KE.A.Q.UGI.N.Y.VALHA.GUQS----..I..VTKLD..TTQ 234
W1-A1           159 DH...T.N.GSE.......V..K.TS.H.TV.D..KE.A.Q.UGI.N.Y.VALHA.GUQS----..I..VTKLD..TTQ 234
W1-A2           159 DH...T.N.GSE.......V...K.TS.H.TV.D..KE.A.Q.UGI.N.Y.VALHA.GUQS----..I..VTKLD..TTQ 234
W1-11           159 DH...T.N.GSE.......V..K.TS.H.TV.D..KE.A.H.UGI.N.Y.VALHA.GUQS----..I..VTKLD..TTQ 234
SK1-15          159 DH...T.N.GSE.......V...K.TS.H.TV.D..KE.A.Q.UGI.N.Y.VALHA.GUQS----..V..VTLLD..TTP 234
SK1-9           159 DH...T.N.GSE.......V..K.TS.H.TV.D..KE.A.Q.UGI.N.Y.VALHA.GUQS----..V..VTLLD..TTP 234
W1-4            159 DH...T.N.GSE.......V...K.TS.H.TV.D..KE.A.Q.UGI.N.Y.VALHA.GUQS----..V..VTLLD..TTP 234

250       260       270       280       290       300       310       320
                   ...|....|....|....|....|....|....|....|....|....|....|....|....|....|....|....|
patent/AAK25847 229 GHCCCASPAPACCAPACCAPACHDQPQCPQGQQPPQCQQPPQCQQPPQGQQPPQG-HDQQCQQPPQCQQPPQCN  307
patent/AAK12389 236 ------------------------------..SA.RTTTITT----RTTTRTTT--KTL.TINRKCSAKITA..YKCC--- 278
SK1-14          234 ------------------------------K.SN.TTAARTTRTTARTTARTTTRTKTL.TN..RCSSKITA..YKCC--- 281
SK1-11          234 ------------------------------K.SN.TTAARTTRTTARTTARTTTRTKTL.TN..RCSSKITA..YKCC--- 281
SK1-2           234 ------------------------------K.SN.TTAARTTRTTARTTARTTTRTKTL.TN..RCSSKITA..YKCC--- 281
SK1-12          234 ------------------------------K.SN.TTAARTTRTTARTTARTTTRTKTL.TN..RCSSKITA..YKCC--- 281
SK1-18          234 ------------------------------K.SN.TTAARTTRTTARTTARTTTRTKTL.TN..RCSSKITA..YKCC--- 281
SK1-20          234 ------------------------------K.SN.TTAARTTRTTARTTARTTTRTKTL.TN..RCSSKITA..YKCC--- 281
W1-A1           234 ------------------------------K.SN.TTAARTTRTTARTTARTTTRTKTL.TN..RCSSKITA..YKCC--- 281
W1-A2           234 ------------------------------K.SN.TTAARTTRTTARTTARTTTRTKTL.TN..RCSSKITA..YKCC--- 281
W1-11           234 ------------------------------K.SN.TTAARTTRTTARTTARTTTRTKTL.TN..RCSSKITA..YKCC--- 281
SK1-15          234 ------------------------------K.SS.ATSAA------RTTTRTTTRTKSL.TNY.KCSARITA..YKCC--- 277
SK1-9           234 ------------------------------K.SS.ATSAA------RTTTRTTTRTKSL.TNY.KCSARITA..YKCC--- 277
W1-4            234 ------------------------------K.SS.ATSAA------RTTTRTTTRTKSL.TNY.KCSARITA..YKCC--- 277

330       340       350       360       370       380       390       400
                   ...|....|....|....|....|....|....|....|....|....|....|....|....|....|....|....|
patent/AAK25847 308 DQQQCGQQPPQPQGPQGPQGGNPGGSDFHNUNQGGSPUGGNQGGSPUGGNQGGNPUGGNQGGSPUGGNQGGSPUGCQCNQGGNPU 387
patent/AAK12389 278 ---------------SD.NCVVYYTDKD.------------------------------T..VE.----Q.  301
SK1-14          281 ---------------S..NCEIVYTDDD.------------------------------T..VE.----E.  304
SK1-11          281 ---------------S..NCEIVYTDDD.------------------------------T..VE.----E.  304
SK1-2           281 ---------------S..NCEIVYTDDD.------------------------------T..VE.----E.  304
SK1-12          281 ---------------S..NCEIVYTDDD.------------------------------T..VE.----E.  304
SK1-18          281 ---------------S..NCEIVYSDDD.------------------------------T..VE.----E.  304
SK1-20          281 ---------------S..NCEIVYTDDD.------------------------------T..VE.----E.  304
W1-A1           281 ---------------S..NCEIVYTDDD.------------------------------T..VE.----E.  304
W1-A2           281 ---------------S..NCEIVYTDDD.------------------------------T..VE.----E.  304
W1-11           281 ---------------S..NCEIVYTDDD.------------------------------T..VE.----E.  304
SK1-15          277 ---------------SD.NCVVYYTDDD.------------------------------T..VE.----E.  300
SK1-9           277 ---------------SD.NCVVYYTDDD.------------------------------T..VE.----E.  300
W1-4            277 ---------------SD.NCVVYYTDDD.------------------------------T..VE.----E.  300
```

Fig. 3(b) cont.

```
                    420       430       440       450       460       470
                ....|....|....|....|....|....|....|....|....|....|....|....|..
patent/AAR26947 389 CCHQCCSPWGGWQGGWPGGWQUGAPQHAAAPQSAAAPQHASDGGHCASLUGQCG----------GOGYHG 448
patent/AAR12989 302 C.--------------------CGVH.CSGKIT.QGYRCCSDPR.UVYYTDDD...........--.RU. 338
SK1-14          305 C.--------------------CCLHRCSSKIT.QGYRCCSDP..UVYYTDDDRLLLAPHGVTDDD.RU. 354
SK1-11          305 C.--------------------CCLHRCSSKIT.QGYRCCSDP..UVYYTDDD...........--.RU. 341
SK1-2           305 C.--------------------CCLHRCSSKIT.QGYRCCSDP..UVYYTDDD...........--.RU. 341
SK1-12          305 C.--------------------CCLHRCSSKIT.QGYRCCSDP..UVYYTDDD...........--.RU. 341
SK1-18          305 C.--------------------CCLHRCSSKIT.QGYRCCSDP..UVYYTDDD...........--.RU. 341
SK1-20          305 C.--------------------CCLHRCSSKIT.QGYRCRSDP..UVYYTDDD...........--.RU. 341
W1-21           305 C.--------------------CCLHRCSSKIT.QGYKCRSDP..UVYYTDDD...........--.RU. 341
W1-22           305 C.--------------------CCLHRCSSKIT.QGYRCCSDP..UVYYTDDD...........--.RU. 341
W1-11           305 C.--------------------CCLHRCSSKIT.QGYRCCSDP..UVYYTDDD...........--.RU. 341
SK1-15          301 C.--------------------CGVHQCSSKITSQGYKCCSDP..UVYYTDDD...........--.RU. 337
SK1-9           301 R.--------------------CGVHQCSSKITSQGYKCCSDP..UVYYTDDD...........--.RU. 337
W1-4            301 C.--------------------CGVHQCSSKITSQGYKCCSDP..UVYYTDDD...........--.RU. 337
```

Fig. 4(a)

```
                    10         20         30         40         50         60         70         80
               ....|....|....|....|....|....|....|....|....|....|....|....|....|....|....|....|
U66253/Np    1 GCTCCACCTCTTGCCCAATGGGCCGGCCGATGGCACTTCGGCCGGTTTCGGAGGACGCTTCCGAGGAGGCTTCGGTGGTAA  80
sk1-6        1 A..GTT...AAG..........T..TTTTG.T.........A..C.......---...T..T..---........A...   74
w1-6         1 A..CTT...AAG..........T..TTTTG.T.........A..C.......---...T..T..---........A...   74

90        100        110        120        130        140        150        160
               ....|....|....|....|....|....|....|....|....|....|....|....|....|....|....|....|
U66253/Np   81 TAACAACGGTGGAGCTGTTACTGGTAATACTAATGGTGGTATTGATGATCAATCTGGAGAATCTATCCGTATTATGCCAA 160
sk1-6       75 CCGT..TAA...------C.A.AA.....AC.........A..T..C.GT...A..T..TA..G.TAAA........TG 148
w1-6        75 CGGT..TAA...------C.A.AA.....AC.........A..T..C.GT...A..T..TA..G.TAAA........TG 148

170        180        190        200        210        220        230        240
               ....|....|....|....|....|....|....|....|....|....|....|....|....|....|....|....|
U66253/Np  161 TGGGTGATTCTATCACATTTGGTATTGGTGAAACTGGTGGTTACAGAAAGTACCTTTACAGCGATTTAACCAAACAAGGT 240
sk1-6      149 .T............T......GAA........GA.....A............T.........T.CC.....TC..A..... 228
w1-6       149 .T............T......GAA........GA.....A............T.........T.CC.....TC..A..... 228

250        260        270        280        290        300        310        320
               ....|....|....|....|....|....|....|....|....|....|....|....|....|....|....|....|
U66253/Np  241 TACAAAATTGATATGGTTGGTCCAGAAGGATCAAGTCGTGCTACCGAAAATGGTATTACATTTGATGACAATCACGCTGG 320
sk1-6      229 ..T.............A........G.....C.ACA.....T.A.CT.........CA..A......T...A.T..... 308
w1-6       229 ..T.............A........G.....C.ACA.....T.A.CT.........CA..A......T...A.T..... 308

330        340        350        360        370        380        390        400
               ....|....|....|....|....|....|....|....|....|....|....|....|....|....|....|....|
U66253/Np  321 TTACAGTGGATACACCATCAAAAACGGTCTCGAATTCTTCAGAGGTCTTGAAGGAAATGGAAGTTTATATGATGTCCTTA 400
sk1-6      309 ..........T.CAA..T...G.AAT..CA..GT.GGGGTCA.CAA.AA.GT..TG.A..C........CA..AAA.... 388
w1-6       309 ..........T.CAA..T...G.AAT..CA..GT.GGGGTCA.CAA.AA.GT..TG.A..C........CA..AAA.... 388

410        420        430        440        450        460        470        480
               ....|....|....|....|....|....|....|....|....|....|....|....|....|....|....|....|
U66253/Np  401 AATTGAAACATTCTGTTAAATTAGCTAAACCAGATATCATTCTTCTTATCATTGGTACCAATGATATGTCCGGAAATCAC 480
sk1-6      389 .GACT..GA..C.......GCA.T..C..................T.........A...CC....GT 468
w1-6       389 .GAGT..GA..G.......GCA.T..C..................T.........A...CC....GT 468

490        500        510        520        530        540        550        560
               ....|....|....|....|....|....|....|....|....|....|....|....|....|....|....|....|
U66253/Np  481 TCTACCCAATCTTGTACTAATGATCTTCATCATCTTTTACATTATGTTATTGGTCAAATGCCATCTCATTGTACTATCTT 560
sk1-6      469 ..A.TGG.TG.....G.C.......G..C.............A.GC....A..T......G.CA..A...T...... 548
w1-6       469 ..A.TGG.TG.....G.C.......G..C.............A.GC....A..T......G.CA..A...T...... 548

570        580        590        600        610        620        630        640
               ....|....|....|....|....|....|....|....|....|....|....|....|....|....|....|....|
U66253/Np  561 CCTTTCTTCTATTCCAGA-TTTACAAACTA-----ACAACGCCCAAAATGTTCTTTCTTACAACGAAGCAGTTAAGAAGG 634
sk1-6      549 TA.GGG............A.....TGC...CGGTGGT..TT.T....GAA..GC.AA......T.GTA............ 628
w1-6       549 TA.GGG............A.....TGC...CGGTGGT..TT.T....GAA..GC.AA......T.GTA............ 628

650        660        670        680        690        700        710        720
               ....|....|....|....|....|....|....|....|....|....|....|....|....|....|....|....|
U66253/Np  635 TTCTTACCCAATACCAACGAAAGCGTAAGAATCTTACATTTGCTCGATATTCACGGTTCTATGAACGGTATGCTCGATATG 714
sk1-6      629 ...C.GAT......GCTAAT....................G....T......C.T.................T 708
w1-6       629 ...C.GAT......GCTAAT................C....T......C.T.................T 708

730        740        750        760        770        780        790        800
               ....|....|....|....|....|....|....|....|....|....|....|....|....|....|....|....|
U66253/Np  715 AGTTCTGATAAGGTTCATCCAAGTGGATCTCGTTACAAGAAGATGGGTGACTACTTTGCTACAGTTGTTGACAGCTTTAT 794
sk1-6      709 G..GG...CC.AC....C........AA......T..A..A..T...A...T..GG...GG......C...TGAA.ACC. 788
w1-6       709 G..GG...CC.AC....C........AA......T..A..A..T...A...T..GG...GG......C...TGAA.ACC. 788

810        820        830        840        850        860        870        880
               ....|....|....|....|....|....|....|....|....|....|....|....|....|....|....|....|
U66253/Np  795 TAAGGAAAATCCAGACTTCAGAGGTACCAGTTCCTCTAACAAGCCCACTACCACCAAGCCCACTACCCCAACCACCGGTA 874
sk1-6      789 .C.---.TC.ATCA.A.CT.ATAACGGTG..AAGGAAG.TG.AA..GG..GTGGT.GT.G..A.GGTGA.GTAGAACT.. 865
w1-6       789 .C.---.TC.ATCA.A.CT.ATAACGGTG..AACGAAG.TG.AA..GG..GTGGT.GT.G..A.GGTGA.GTAGAACT.. 865

890        900        910        920        930        940        950        960
               ....|....|....|....|....|....|....|....|....|....|....|....|....|....|....|....|
U66253/Np  875 ATACCACTTGTTCCGCTAAGATTACTAGCCAAGGCTACAAGTGTTGTTCTGCTAGCTGTGTGTTGTCTACACTGACAAC 954
sk1-6      866 G..A---.......AAG...A.........A.....T....A.........AAG.AT.....A..CA..........TGC. 942
w1-6       866 G..A---.......AAG...A.........A.....T....A.........AAG.AT.....A..CA..........TG.. 942

970
               ....|....|....|
U66253/Np  955 GACGGAGATTGGGGC 969
sk1-6      943 ..T..TA.A.....T 957
w1-6       943 ..T..TA.A.....T 957
```

Fig. 4(b)

```
                         10        20        30        40        50        60        70        80
                    ....|....|....|....|....|....|....|....|....|....|....|....|....|....|....|....|
AAB69092/BTS     1  APALAQNGGGWDFGGFGGGFGGGFGGNNNGGAVTGNTNGGIDDQSGKSIRIHPHGDSITFGIGETGGYRKYLYSDLTKQG 80
SK1-6            1  ..TV.K.....FG.......-...-..D.G.N.--NN.N...NVAV..DTVK...V........E..R.........A..QR. 76
W1-6             1  ..TV.R.....FG.......-...-..D.G.N.--NN.N...NVAV..DTVK...V........E..R.........A..QR. 76

90       100       110       120       130       140       150       160
                    ....|....|....|....|....|....|....|....|....|....|....|....|....|....|....|....|
AAB69092/BTS    81  YKIDHVGPEGSSRATENGITFDDNHAGYSGYTIKNGLEFFRGLEGNGSLYDVLKLKHSVKLAKPDIILLIIGTNDHSGNH 160
SK1-6           77  ............NS.SA...QY...N......FQ..EIPGWGQQQG.E....NK..S.NA..QSQ............TA.R 156
W1-6            77  ............NS.SA...QY...N......FQ..EIPGWGQQQG.E....NK..S.NA..QSQ............TA.R 156

170       180       190       200       210       220       230       240
                    ....|....|....|....|....|....|....|....|....|....|....|....|....|....|....|....|
AAB69092/BTS   161  STQSCTNDLHDLLDYVIGKHPSHCTIFLSSIPDLQTN--NAQNVLSYNEAVKKVVSHYQGKGKNVRFADIHGCHNGHADH 238
SK1-6          157  .HDA.A...RA....ML.D..ANSI..HG...EFTAYGG.S.RIAN..GT....AD..AN.........V...L.....I 236
W1-6           157  .HDA.A...RA....ML.D..ANSI..HG...EFTAYGG.S.RIAN..GT....AD..AN.........V...L.....I 236

250       260       270       280       290       300       310       320
                    ....|....|....|....|....|....|....|....|....|....|....|....|....|....|....|....|
AAB69092/BTS   239  SSDKVHPSGSGYKKHGDYFATVVDSFIKENPDFRGTSSSNKATTTKATTPTTGNTTCSAKITSQGYKCCSASCVVVYTDN 318
SK1-6          237  GG.QL....N....T.NFW.G...KYLQSIKSNN.--GKEDE.GSGSCNGKVRLSN..S...R.......KN...T...A 314
W1-6           237  GG.QL....N....I.NFW.G...KYLQSIKSNN.--GKEDE.GSGSCNGEVELSN..S...R.......KN...I...D 314

....|
AAB69092/BTS   319  DGDWG 323
SK1-6          315  ..K.. 319
W1-6           315  ..K.. 319
```

RECOMBINANT XYLANASES DERIVED FROM ANAEROBIC FUNGI, AND THE RELEVANT SEQUENCES, EXPRESSION VECTORS AND HOSTS

FIELD OF THE INVENTION

The present invention relates to novel recombinant xylanases derived from anaerobic fungi, such as *Neocallimastix frontalis* and *N. patriciarum*. The xylanases of the invention are thermo- and alkaline pH-tolerable, and highly specific for xylans with high activity. The present invention also relates to the relevant DNA sequences encoding said xylanases, as well as the hosts carrying said DNA sequences.

BACKGROUND OF THE INVENTION

Xylanase degrades the polysaccharide, xylan, which is the major constitute of hemicelluloses in plants. Xylan is most abundant renewable resource next to cellulose in the world, which is a hetero-polysaccharide having β-1,4-D-pyranoxylose-linked backbone and various substituted side chains. Due to its complicated structure, it needs an enzyme-degrading system for complete breakdown of xylan. These enzymes include the backbone degrading enzymes: Endo, β-1,4 xylanase (EC 3.2.1.8) and β-xylosidase (EC 3.2.1.37); and side chain degrading enzymes: α-L-arabinofuranosidase (EC 3.2.1.55), α-glucuronidase (EC 3.2.1.139), and acetylxylan esterase (EC 3.1.1.72) (Q. K. Beg, M. Kapoor, L. Mahajan, and G. S. Hoondal. Microbial xylanases and their industrial applications: a review. *Appl Microbiol Biotechnol* (2001) 56:326-338) Among these enzymes, endo β-1,4 xylanase contributes for the most part of xylan degradation.

Endo-xylanases are enzymes that randomly cleave the β(1-4) linkages between xylose residues making up the backbone of xylans, a prevalent form of hemicellulose found predominantly in plant primary and secondary cell walls. Many prior arts, such as U.S. Pat. No. 5,948,667 (published on Sep. 7, 1999), U.S. Pat. No. 6,300,114 (patented on Oct. 9, 2001), U.S. Pat. No. 5,824,533 (patented on Oct. 20, 1998) and WO 93/25693 (published on Dec. 23, 1993), etc, have disclosed various xylanases and their uses. The known applications of xylanases are numerous. For instance, the treatment of forages with xylanases (along with cellulases) to increase the rate of acid production, thereby ensuring better quality silage and improvement in the subsequent rate of plant cell wall digestion by ruminants has been described. Xylanases can be used to treat rye, and other cereals with a high arabinoxylan content to improve the digestibility of cereal by poultry and swine. Xylanases can be used in bioconversion involving the hydrolysis of xylan to xylooligosaccharides and xylose which may serve as growth substrates for microorganisms. This could involve simultaneous saccharification and fermentation. Xylanases can be used in biopulping to treat cellulose pulps to remove xylan impurities or to produce pulps with different characteristics. In some cases they can be applied to reduce the amount of chlorine needed to bleach the pulp and reduce the energy needed for refining pulp. Further, xylanases are useful in the retting of flax fibers, the clarification of fruit juices, the preparation of dextrans for use as food thickeners and the production of fluids and juices from plant materials.

Commercially available xylanases and their activities and purposes are reviewed in "Q. K. Beg, M. Kapoor, L. Mahajan, and G. S. Hoondal. Microbial xylanases and their industrial applications: a review. *Appl Microbiol Biotechnol* (2001) 56:326-338".

Particularly, it was reported that the pretreatment of unbleached kraft pulp with xylanase results in a reduced consumption of chemicals for bleaching process. Prior arts have also disclosed that the xylanase pretreatment is useful in conjunction with bleaching sequences consisting of $Cl_2$, $ClO_2$, $H_2O_2$ and $O_3$. As a direct result of the better bleachability of the pulp after such a xylanase treatment, there is a reduction of the subsequent consumption of bleaching chemicals, which when chloride containing chemicals are used, leads to a reduced formation of environmentally undesired organo-chlorine compounds. Also as a direct result of the better bleachability of pulp after a xylanase treatment, it is possible to produce a product with a final brightness where such brightness would otherwise be hard to achieve (such as totally chlorine free (TCF) bleaching using peroxide). Because of the substrate specificity of the xylanase enzyme, cellulose fibers are not harmed and the strength properties of the product are well within acceptable limits.

However, it is not as simple as merely adding a xylanase treatment step. Most commercial xylanases designed for pulp bleaching are not very thermotolerant, especially when neutral or alkaline pH conditions are used. In practice, xylanases are generally inefficient or inactive at temperatures higher than 60° C. Therefore, the recombinant xylanase specifically disclosed in WO 9325693, which is derived from *Neocallimastix patriciarum* and designated XYLA and has a specific activity of 5980 U/mg, could not satisfy the requirements of pulp and paper manufacturers.

A xylanase that is active at an alkaline pH would decrease the need to acidify the pulp prior to xylanase treatment. In addition, the temperatures of many modern kraft cooking and bleaching processes are relatively high, well above 50° C., that is unsuitable for many of the commercial bleaching enzymes. Accordingly, a need exists for thermostable xylanase preparations that are stable at alkaline pH's for use in wood pulp bleaching processes. In order to obtain thermostable xylanases, U.S. Pat. No. 6,300,114 produced proteins originating from actinomycetes in filamentous fungi such as *Aspergillus* or *Trichoderma*.

The ruminants are glorified by their ability to digest fibrous plant materials. Ruminants themselves do not produce fiber-degrading enzymes, but they harbor bacteria, fungi, and protozoa which can digest fiber to support hosts' survival (Russell, J. B., and J. L. Rychlik. 2001. Factors that alter rumen microbial ecology. Science 292:1119-22). The rumen ecosystem comprises a diverse population of anaerobic bacteria, fungi, and protozoa defined by the intense selective pressures of the ruminal environment. The ruminal microbes generally become the high activity fiber-degradation resource. Up to now, there are many fiber-degradation genes isolated from rumen (Selinger, B. L., C. W. Forsberg, and K. J. Cheng. The rumen: A unique source of enzymes for enhancing livestock production. Anaerobe 2:263-284 (1996)).

However, up to now, the xylanase relevant genes isolated from rumen were obtained by first constructing a cDNA gene data base and then screening the genes contained therein with xylan relevant bases (Durand, R., C. Rascle, and M. Fevre. Molecular characterization of xyn3, a member of the endoxylanase multigene family of the rumen anaerobic fungus *Neocallimastix frontalis*. Curr Genet Vol. 30 Issue 6 (1996) pp 531-540). Through such a known method, the xylanase gene sequences isolated from ruminal fungi lack intron. Anyway, such a known method is quite time-consuming and inefficiency. Without constructing said cDNA gene data base, the present invention directly uses the DNA from ruminal fungi as a template and adopts a suitable specific primer to proceed with PCR. In such a way, the xylanase gene sequences can be rapidly obtained. Furthermore, some new xylanases expressed by the gene sequences obtained in this way are quite active under high temperature and alkaline reaction condition and have high specific activity. These new recombinant xylanases may be produced by prokaryotic or eukaryotic expression systems.

All references cited herein are incorporated herein by reference.

SUMMARY OF THE INVENTION

The present invention relates inter alia to recombinant xylanases derived from ruminal microbes, preferably anaerobic fungi, such as *Neocallimastix frontalis* and *N. patriciarum*, by using an appropriate primer to carry out polymerase chain reaction (PCR). Xylanases in accordance with the invention are thermo- and alkaline pH-tolerable and have a significantly high specific activity, as compared with those disclosed in the prior arts. Especially, Xynsk1-9$^E$ of SEQ ID NO. 26 exhibits the highest specific activity 10371.04 U/mg protein after reacting in a substrate of 1% oat spelt xylan at 70° C. and pH 6 for 3 minutes.

Xylanases in accordance with the invention may have no significant residual activity against carboxymethylcellulose and barley β-glucan, in contrast to many known xylanases. The former property is particularly useful in the pulp and paper industry, as the enzyme can remove xylan and dissociate lignin from plant fiber without damaging cellulose fiber.

It is further an object of this invention to provide recombinant vectors comprising a DNA sequence encoding a xylanase according to the present invention. Preferably, the xylanase is derived from *Neocallimastix frontalis* or *N. patriciarum*. The gene of interest may preferably be placed under the control of (i.e., operably linked to) certain control sequences such as promoter sequences provided by the vector (which integrate with the gene of interest). If desired, such control sequences may be provided by the host's chromosome as a result of the locus of insertion.

Expression control sequences on an expression vector will vary depending on whether the vector is designed to express a certain gene in a prokaryotic or eukaryotic host (for example, a shuttle vector may provide a gene for selection in bacterial hosts) and may additionally contain transcriptional elements such as, enhancer elements, termination sequences, and/or translational initiation and termination sites.

It is further an object of this invention to provide culture medium from the culture of hosts, into which said recombinant vectors have been transformed. Preferably the host is a prokaryotic expression host, such as *Escherichia coli*, or an eukaryotic expression host, such as *Pichia methanolica*. More preferably the host is *Pichia methanolica*.

It is further an object of this invention to provide primers and probes for use in xylanase gene amplification, which are characterized by having a sequence of aactgttgctaaggcccaatggggt or accccatttaccatcgtcatcagtg.

BRIEF DESCRIPTION OF THE DRAWINGS

FIGS. 3(*a*) and 3(*b*) show DNA sequence alignment result and amino acid sequence alignment result, respectively. The amino acid sequence AAE25847 of a xylanase obtained from *N. patriciarum* is known from U.S. Pat. No. 5,948,667. The DNA sequence U57819 and the amino acid sequence AAE12389 of a xylanase isolated from *Orpinomyces sp.* PC-2 are known from U.S. Pat. No. 5,824,533.

FIGS. 4(*a*) and 4(*b*) show DNA sequence alignment result and amino acid sequence alignment result, respectively. DNA sequence (U66253) and amino acid sequence (AAB69092) of acetylxylan esterase (ETS) isolated from *N. patriciarum* are published in GenBank.

FIG. 7(*b*) shows optimal pH of Xynsk1-9$^E$ and Xynsk1-9$^P$ separately expressed in *E. coli* (●) and *P. methanolica* (○).

DEPOSIT

*Pichia methanolica* PXYNsk1-9, carrying the xynsk1-9 gene (SEQ ID NO: 12) was deposited with the American Type Culture Collection, 10801 University Blvd. Manassas, Va. 20110-2209, on Aug. 20, 2002 and assigned accession number ATCC PTA-4605.

DETAILED DESCRIPTION OF THE INVENTION

The present invention relates inter alia to recombinant xylanases derived from ruminal microbes, preferably anaerobic fungi, which are obtained by using an appropriate primer to carry out polymerase chain reaction (PCR). Examples of anaerobic fungi, which may be alimentary tract (particularly rumen) fungi, include: *Neocallimastix* spp., such as *N. patriciarum, N. frontalis, N. hurleyensis* and *N. stanthorpensis*; *Sphaeromonas* spp., such as *S. communis*; *Caecomyces* spp., such as *C. equi*; *Piromyces* spp., such as *P. communis, P. equi, P. dwnbonica, P. lethargicus* and *P. mat*; *Ruminomyces* spp., such as *P. elegans*; *Anaeromyces* spp., such as *A. mucronatus* and *Orpinomyces* spp., such as *O. bovis* and *O. joyonii*. *Neocallimastix* spp., particularly *Neocallimastix frontalis* and *N. patriciarum*, are preferred.

The preferred recombinant xylanases according to the present invention, which were derived from *Neocallimastix frontalis* or *N. patriciarum*, include those of SEQ ID Nos. 16-27 and 32-33. The recombinant xylanase, Xynsk1-9$^E$, of SEQ ID NO. 26 is particularly preferred.

Xylanases in accordance with the invention are thermo- and alkaline pH-tolerable and have a high specific activity, which may be significantly higher than those disclosed in the prior arts. Especially, Xynsk1-9$^E$ of SEQ ID NO. 26 exhibits the highest specific activity 10371.04 U/mg protein after reacting in a substrate of 1% oat spelt xylan at 70° C. and pH 6 for 3 minutes.

Figure 8:
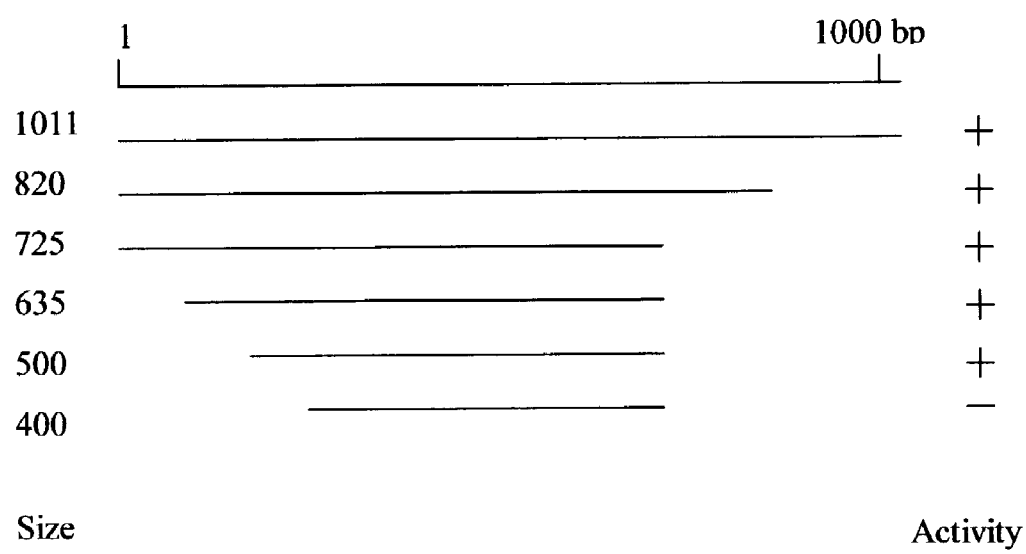
FIG. 8 schematically represents the deletion and activity analysis in connection with the location of the cloned xylanase genes sk1-9.

The xylanases according to the present invention are originally obtained by using specific primers designed from the xylanase gene or amino acid sequences published in GenBank, and using the DNAs of anaerobic fungi isolated from the rumens of Water buffalo (*Bubalus befullus*) and Formosan Sika Deer (*Cervus Nippon* taiwanus) as DNA templates of PCR. The designed primers do not need to amplify the whole xylanase gene sequence, because xylanase gene residues (namely, incomplete xylanase gene sequence) obtained from rumen may still exhibit enzymatic activity as known from the prior arts (Durand, R., C. Rascle, and M. Fevre. 1996. Molecular characterization of xyn3, a member of the endoxylanase multigene family of the rumen anaerobic fungus *Neocallimastix*; Fanutti, C., T. Ponyi, G. W. Black, G. P. Hazlewood, and H. J. Gilbert. 1995. The conserved noncatalytic 40-residue sequence in cellulases and hemicellulases from anaerobic fungi functions as a protein docking domain. J Biol Chem 270:29314-22.). As proven by the present invention hereinafter, incomplete gene sequence may also exhibit enzymatic activity (see FIG. 8). The primers used in this invention are preferably characterized by having a sequence of aactgttgctaaggcccaatggggt or accccatttaccatcgtcatcagtg or the analogues. Obtaining DNA sequences from ruminal microbes and the PCR can be conducted according to the teachings contained in the examples below and in view of what is generally known in the art, and readily adjusted by a person skilled in this art without deviation of the spirit of this invention.

As far as large-scale expression of recombinant protein is concerned, since the amino acid sequences of the xylanases according to the present invention and the relevant DNA sequences have been identified by this application, xylanases in accordance with the invention may be prepared by any suitable means. While bulk fermentation of the transformed hosts may be undertaken, and polypeptide synthesis by the techniques of organic chemistry may be attempted, the method of preparation of choice will generally involve recombinant DNA technology. A xylanase of the present invention will therefore for preference be the expression product of heterologous xylanase-encoding DNA in an eukaryotic expression host or a prokaryotic expression host. The eukaryotic expression host is preferred, because the xylanase genes according to the present invention come from eukaryotic cells. The transformed hosts are cultivated under the known conditions suitable for the customarily used hosts, the desired enzymes are contained in the hosts or secreted from the hosts into the culture medium, and the enzyme preparation is recovered from said culture medium by methods known in the art.

The enzyme preparation is the culture medium with or without transformed host cells, or is recovered from the same by the application of methods well known in the art. For example, when a eukaryotic expression host, such as *Pichia methanolica*, is used, because the xylanase enzymes are secreted into the culture media, it is an advantage of the invention that the enzyme preparations of the invention may be utilized directly from the culture medium with no further purification. If desired, such preparations may be lyophilized or the enzymatic activity otherwise concentrated and/or stabilized for storage. Once a eukaryotic expression host is used, the enzyme preparations of the invention are very economical to provide and use because (1) the enzymes may be used in a crude form; isolation of a specific enzyme from the culture fluid is unnecessary and (2) because the enzymes are secreted into the culture medium, only the culture medium need be recovered to obtain the desired enzyme preparation; there is no need to extract an enzyme from the hosts. However, if a prokaryotic expression host, such as *E. coli*, is used, it is advisable to extract an enzyme from the host.

If desired, an expressed protein may be further purified in accordance with conventional conditions, such as extraction, precipitation, chromatography, affinity chromatography, electrophoresis, or the like.

It is also known that often less than a full length protein has the function of the complete protein, for example, a truncated protein lacking an N-terminal, internal or a C-terminal portion often has the biological and/or enzymatic activity of the complete natural protein. Those of ordinary skill in the art know how to make truncated proteins and proteins with internal deletions. In the present invention, the function of a truncated xylanase protein or an internally deleted xylanase protein can be readily tested using the xylanase assay described herein below and in view of what is generally known in the art.

Substituted and truncated xylanase derivatives which retain substantially the same the enzymatic activity of the xylanase specifically disclosed herein are considered equivalents of the exemplified xylanase and are within the scope of the present invention, particularly where the specific activity of the substituted or truncated xylanase derivative is at least about 10% of the specifically exemplified xylanase. The skilled artisan can readily measure the activity of a truncated or substituted xylanase using the assay procedures taught herein and in view of what is generally known in the art.

According to a second aspect of the invention, there is provided isolated or recombinant DNA molecules encoding xylanases of the present invention. The DNA sequences preferably include the xylanase-encoding region (CDS, protein coding sequence). Genetic variants include hybrid DNA sequences containing the xylanase CDS fused to regulatory regions such as promoter, leader peptide and terminator signals, originating from homologous or heterologous sources. Genetic variants also include DNA sequences encoding mutant xylanase proteins and degenerate DNA sequences wherein the xylan-degrading activity of the enzyme is retained. The present invention provides the starting material for the construction of "second generation" xylanases, i.e., mutant xylanases with properties that differ from those of the enzymes isolated herein, or DNA sequences (encoding the xylanase CDS) altered to reflect the degeneracy of the genetic code or cross-species variation. Genes can be readily mutated by procedures known in the art (e.g., chemical, site directed, random polymerase chain reaction mutagenesis) thereby creating gene products with altered properties (e.g., temperature or pH optima, specific activity or substrate specificity). The xylanase gene of the present invention can be used also in heterologous hybridization and polymerase chain reaction experiments, directed to isolation of xylanase-encoding genes from other natural sources.

Although a full length copy of natural mRNA is not present in DNA in accordance with this aspect of the invention, it should be understood that the invention is not limited to truncated cDNAs. It is contemplated that some or all of the introns (if any) naturally present in the corresponding wild type gene may be present. However, at least some sequence that is present in the full length cDNA is absent in DNA in accordance with this aspect of the invention. It should also be understood that this aspect of the invention encompasses DNAs encoding full length xylanases according to the present invention; the absent portion of the DNA may be (and in some embodiments preferably is) in the 3' and/or 5' untranslated regions. Substantially full length or truncated xylanases may therefore be produced from DNA in accordance with this aspect of the invention which (a) is substantially missing the 3' untranslated region, or (b) is substantially missing the 5' untranslated region or (c) is substantially missing both the 3' and 5' untranslated regions.

The preferred recombinant DNA in accordance with the invention include those of SEQ ID Nos. 2-13 and 29-30. The recombinant DNA, Xynsk1-9 of SEQ ID NO. 12, is particularly preferred.

Recombinant DNA in accordance with the invention may be in the form of a vector. The vector may for example be a plasmid, cosmid or phage. Vectors will frequently include one or more selectable markers to enable selection of cells transfected (or transformed: the terms are used interchangeably in this specification) with them and, preferably, to enable selection of cells harbouring vectors incorporating heterologous DNA. Appropriate start and stop signals will generally be present. Additionally, if the vector is intended for expression, sufficient regulatory sequences to drive expression will be present. Vectors not including regulatory sequences are useful as cloning vectors; and, of course, expression vectors may also be useful as cloning vectors.

Cloning vectors can be introduced into *E. coli, Pichia methanolica* or another suitable host which facilitates their manipulation. The useful hosts for producing the xylanases of the present invention includes industrial strains of microorganisms, such as *Aspergillus niger, Aspergillus ficcum, Aspergillus awamori, Aspergillus oryzae, Trichoderma reesei, Mucor miehei, Kluyvermoyces lactis, Pichia pastoris, Pichia methanolica, Saccharomyces cerevisiae, Escherichia coli, Bacillus subtilis* or *Bacillus licheniformis*, etc., or plant hosts, such as canola, soybean, corn, potato, etc. All systems employ a similar approach to gene expression. An expression construct is assembled to include the protein coding sequence of interest and control sequences such as promoters, enhancers and terminators. Other sequences such as signal peptide sequences and selectable markers may be included. To achieve extracellular expression of xylanase, the expression construct of the present invention utilizes a secretory signal peptide sequence. The signal peptide sequence is not included on the expression construct if cytoplasmic expression is desired. Transcriptional terminators are included to ensure efficient transcription. Ancillary sequences enhancing expression or protein purification may also be included in the expression construct. The promoter, enhancer, signal peptide and terminator elements are functional in the host cell and provide for efficient expression and secretion of the xylanase.

According to another aspect of the invention, there is therefore provided a host cell transfected or transformed with DNA as described above. Preferably, the host is *E. coli* or *Pichia methanolica*. *Pichia methanolica* is particularly preferred.

Xylanases in accordance with the invention have a number of applications in the food, feed, and pulp and paper industries. The use of xylanases described herein in these industries is included within the scope of the invention. It is believed that the xylanases of the present invention are particularly applicable to the paper and pulp industry.

DEFINITIONS

Throughout this text, a number of terms as used in recombinant DNA technology are defined as follows:

Xylanase. A xylanase is a hemicellulase that cuts the β-1,4 bonds within the xylosic chain of xylan, (xylan is a polymer of D-xylose residues that are joined through β-1,4 linkages). Xylanase activity is synonymous with xylanolytic activity.

A unit of xylanase activity is defined as the quantity of enzyme releasing 1μ mole of product, measured as xylose equivalents, in 1 minute at 37° C.

By an amino acid sequence that is an "equivalent" of a specific amino acid sequence is meant an amino acid sequence that is not identical to the specific amino acid sequence, but rather contains at least some amino acid changes (deletion, substitutions, inversions, insertions, etc) that do not essentially affect the biological activity of the protein as compared to a similar activity of the specific amino acid sequence, when used for a desired purpose. Preferably, an "equivalent" amino acid sequence contains at least 85%-99% homology at the amino acid level to the specific amino acid sequence, most preferably at least 90% and in an especially highly preferable embodiment, at least 95% homology, at the amino acid level.

Enzyme preparation. By "enzyme preparation" is meant a composition containing enzymes that have been extracted from (either partially or completely purified from) a microbe or the medium used to grow such microbe. "Extracted from" means any method by which the desired enzymes are separated from the cellular mass and includes breaking cells and also simply removing the culture medium from spent cells. Therefore, the term "enzyme preparation" includes compositions comprising medium previously used to culture a desired microbe(s) and any enzymes which the microbe(s) has secreted into such medium during the culture.

Homologous. By an enzyme "homologous" to a host of the invention is meant that an untransformed strain of the same species as the host species naturally produces some amount of the native protein; by a gene "homologous" to a host of the invention is meant a gene found in the genome of an untransformed strain of the same species as the host species. By an enzyme "heterologous" to a host of the invention is meant that an untransformed strain of the same species as the host species does not naturally produce some amount of the native protein; by a gene "heterologous" to a host of the invention is meant a gene not found in the genome of an untransformed strain of the same species as the host species.

Cloning vehicle. A plasmid or phage DNA or other DNA sequence (such as a linear DNA) which provides an appropriate nucleic acid environment for the transfer of a gene of interest into a host cell. The cloning vehicles of the invention may be designed to replicate autonomously in prokaryotic and eukaryotic hosts. In fungal hosts such as *Pichia*, the cloning vehicles generally do not autonomously replicate and instead, merely provide a vehicle for the transport of the gene of interest into the *Pichia* host for subsequent insertion into the *Pichia* genome. The cloning vehicle may be further characterized by one or a small number of endonuclease recognition sites at which such DNA sequences may be cut in a determinable fashion without loss of an essential biological function of the vehicle, and into which DNA may be spliced in order to bring about replication and cloning of such DNA. The cloning vehicle may further contain a marker suitable for use in the identification of cells transformed with the cloning vehicle. Markers, for example, are antibiotic resistance. Alternatively, such markers may be provided on a cloning vehicle which is separate from that supplying the gene of interest. The word "vector" is sometimes used for "cloning vehicle."

Expression vehicle. A vehicle or vector similar to a cloning vehicle but which is capable of expressing a gene of interest, after transformation into a desired host.

When a fungal host is used, the gene of interest is preferably provided to a fungal host as part of a cloning or expression vehicle that integrates into the fungal chromosome. Sequences which derive from the cloning vehicle or expression vehicle may also be integrated with the gene of interest during the integration process.

The gene of interest may preferably be placed under the control of (i.e., operably linked to) certain control sequences such as promoter sequences provided by the vector (which integrate with the gene of interest). If desired, such control sequences may be provided by the host's chromosome as a result of the locus of insertion.

Expression control sequences on an expression vector will vary depending on whether the vector is designed to express a certain gene in a prokaryotic or eukaryotic host (for example, a shuttle vector may provide a gene for selection in bacterial hosts) and may additionally contain transcriptional elements such as, enhancer elements, termination sequences, and/or translational initiation and termination sites.

The invention is described in more detail in the following examples, These examples show only a few concrete applications of the invention. It is self evident for one skilled in the art to create several similar applications. Hence the examples should not be interpreted to narrow the scope of the invention only to clarify the use of the invention.

EXAMPLES

Example 1

Obtaining DNA Sequences from Anaerobic Fungi *Neocallimastix frontalis* (sk1) and *N. patriciarum* (w1)

The anaerobic fungi *Neocallimastix frontalis* (sk1) and *N. patriciarum* (w1) were isolated from the rumens of Water buffalo (*Bubalus befullus*) and Formosan Sika Deer (*Cervus Nippon* taiwanus) as described by Orpin, C. G. et al. [Orpin, C. G., and Munri, E. A., Trans. Br. Mycol. Soc. 86: 178181 (1986)]. *Neocallimastix frontalis* (sk1) and *N. patriciarum* (w1) were grown in a rumen fluid-containing medium (Kemp et al, J. Gen. Microbiol. 130: 27-37 (1984)) in the presence of 1% avicel at 39° C. and anaerobic conditions for 48 hr.

The total DNAs of strains *Neocallimastix frontalis* (sk1) and *N. patriciarum* (w1) were extracted as described by Moncalvo et al (Moncalvo, J. M., H. H. Wang, and R. S. Hseu, 1995, Phylogenetic relation-ships in Ganoderma inferred from the internal transcribed spacers and 25S ribosomal DNA sequences, Mycologia 87:223-238). Lyophilized mycelium was ground to a powder in a mortar and pestle. Materials were suspended in 500 µl lysis buffer (0.2 M Tris, 0.25 M NaCl, 0.025 M EDTA, 0.5% SDS (pH 8.5)). After adding 500 µl of phenol/chloroform/isoamyl alcohol (25:24:1), the mixture was mixed well and centrifuged for 15 min. The supernatant was transferred to a clean tube and 0.1 vols. of 3M sodium acetate and 0.6 vols. of isopropanol were added. After mixing, the solution was left to stand for 5 min. The sample was centrifuged for 15 min and drained. The pellet was rinsed with 70% ethanol, briefly dried under vacuum, and then dissolved in 100 µl of TE (10 mM Tris, 1 mM EDTA (pH 8.0)). After a suitable dilution (500×), the DNA solution is used as a template of PCR. PCR is carried out by using an appropriate primer. The primers and their nucleotide sequences as well as their purposes are shown in Table 1. The reaction reagents for use in said PCR are listed in Table 2. The reaction conditions of said PCR are as follows: under 94° C. for 2 minutes, and then successively repeating the following four conditions for 35 times: (1) under 94° C. for 45 seconds (denature DNA), (2) under 50° C. for 45 seconds, (3) under 72° C. for 45 seconds, (4) under 72° C. for 10 minutes.

TABLE 1

Primers used in PCR

| Primers | Sequence (5' → 3') | SEQ ID NO | Purposes |
|---|---|---|---|
| EX4F | aactgttgctaaggcccaatggggt | 34 | Xylanase gene amplification |
| EX3R | accccatttaccatcgtcatcagtg | 35 | Xylanase gene amplification |
| EX4F-E (BamHI) | ggatccactgttgctaaggcccaatggggt | 36 | *E. coli* vector construction |
| EX3R-E (EcoRI) | gaattctcaaccccatttaccatcgtcat | 37 | *E. coli* vector construction |
| EX4F-P (EcoRI) | gaattcgcgactgttgctaaggccc | 38 | *P. methanolica* vector construction |
| EX3R-P (BamHI) | cgcggatccaccccatttaccatcgtcatc | 39 | *P. methanolica* vector construction |

TABLE 2

PCR reagents (25 µl)

| Component | Volume | Final concentration |
|---|---|---|
| 10 × PCR buffer | 2.5 µl | 1× |
| MgCl₂ 15 mM | 2.5 µl | 1.5 mM |
| dNTP 2.5 mM (each) | 2 µl | 0.2 mM |
| Primers 10 µM (each) | 1 µl each | 0.4 µM each |
| Taq DNA polymerase (5 U/µl) | 0.07 µl | 0.014 U/µl |
| dH₂O | 5.93 µl | |
| DNA template | 10 µl | |

Figure 1:
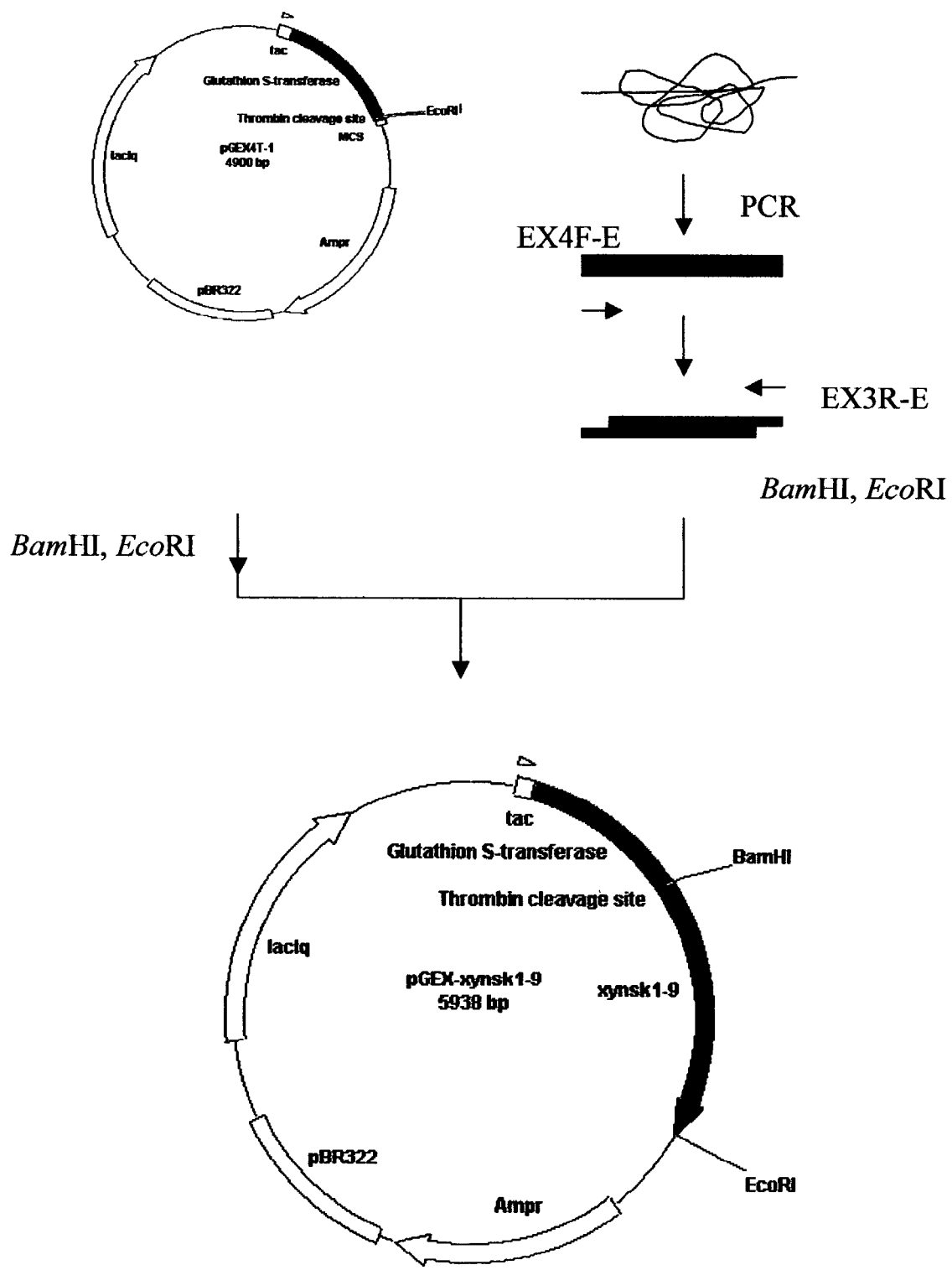
FIG. 1 shows the construction of pGEXxynsk1-9$^E$.
Figure 2:
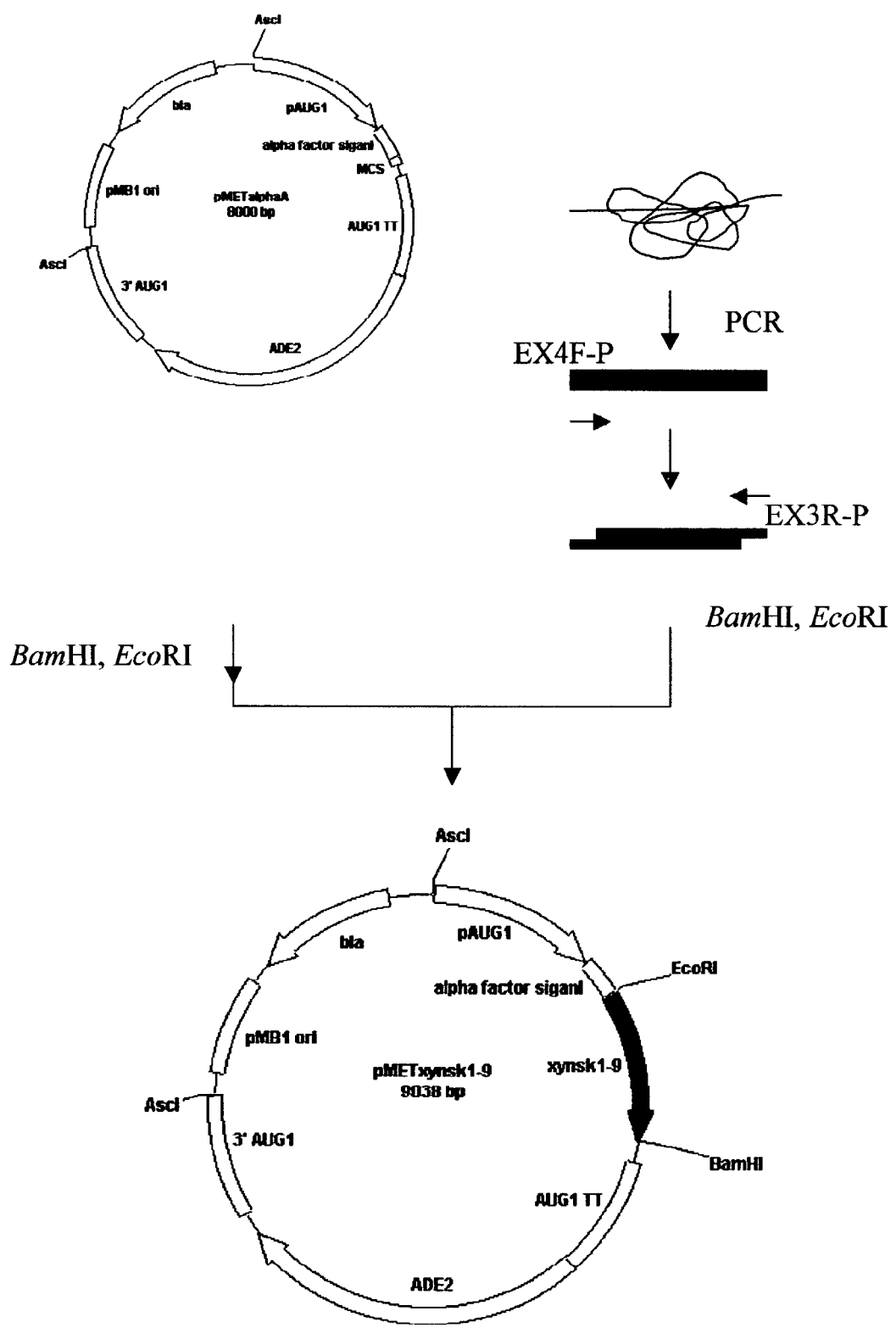
FIG. 2 shows the construction of pMETxynsk1-9$^E$.
Figure 3A:
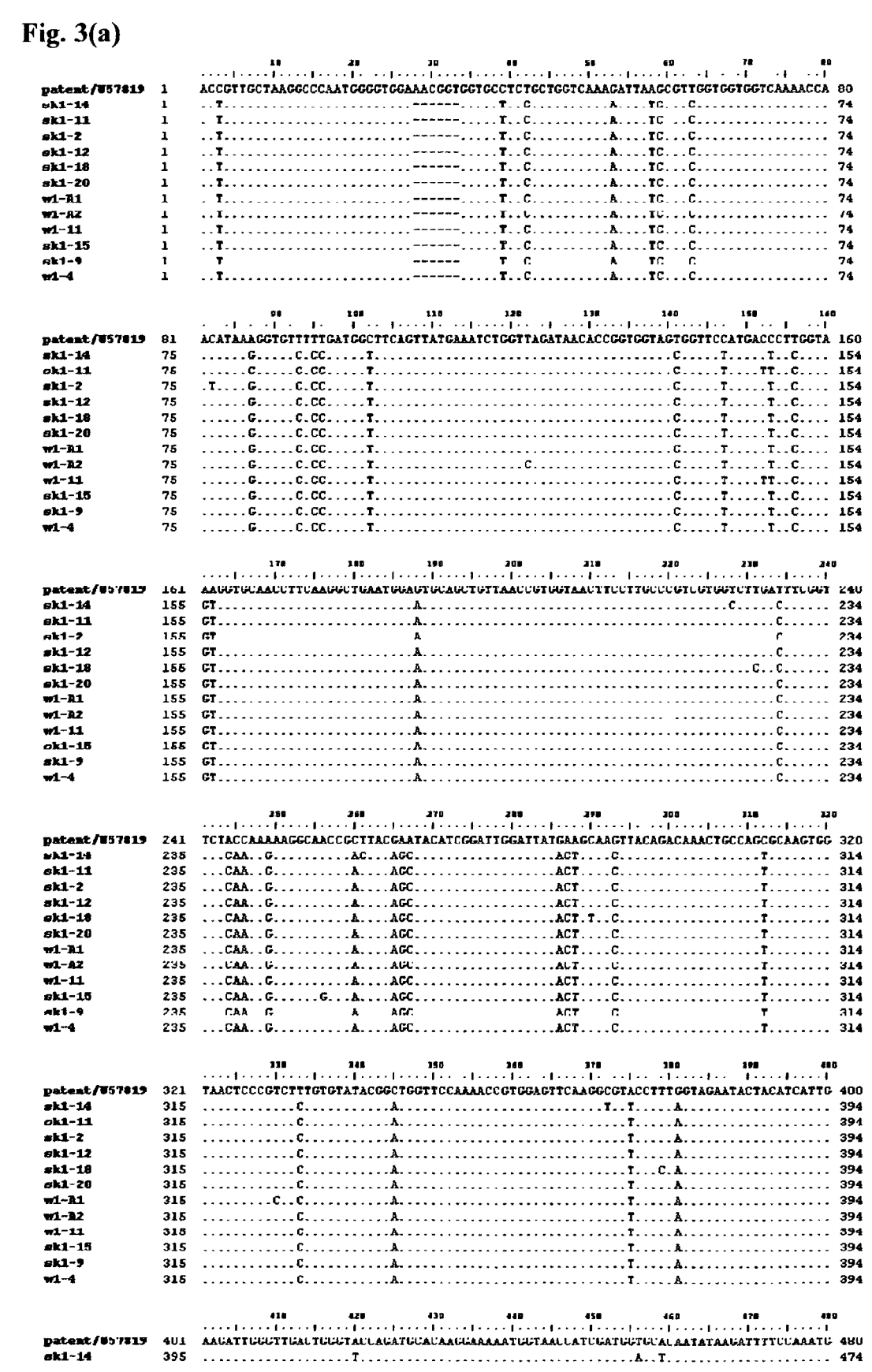
Figure 3A:
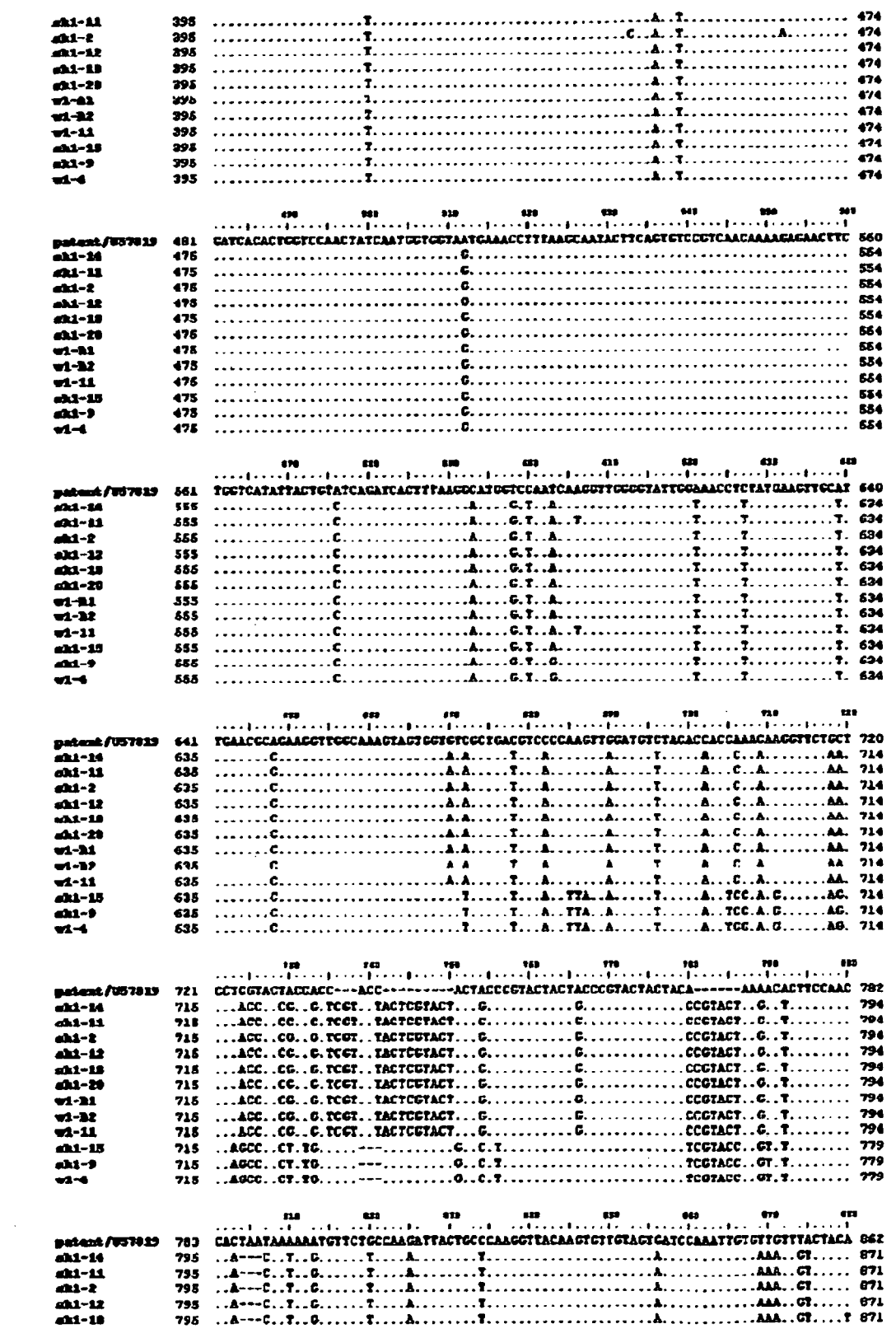
Figure 3A:
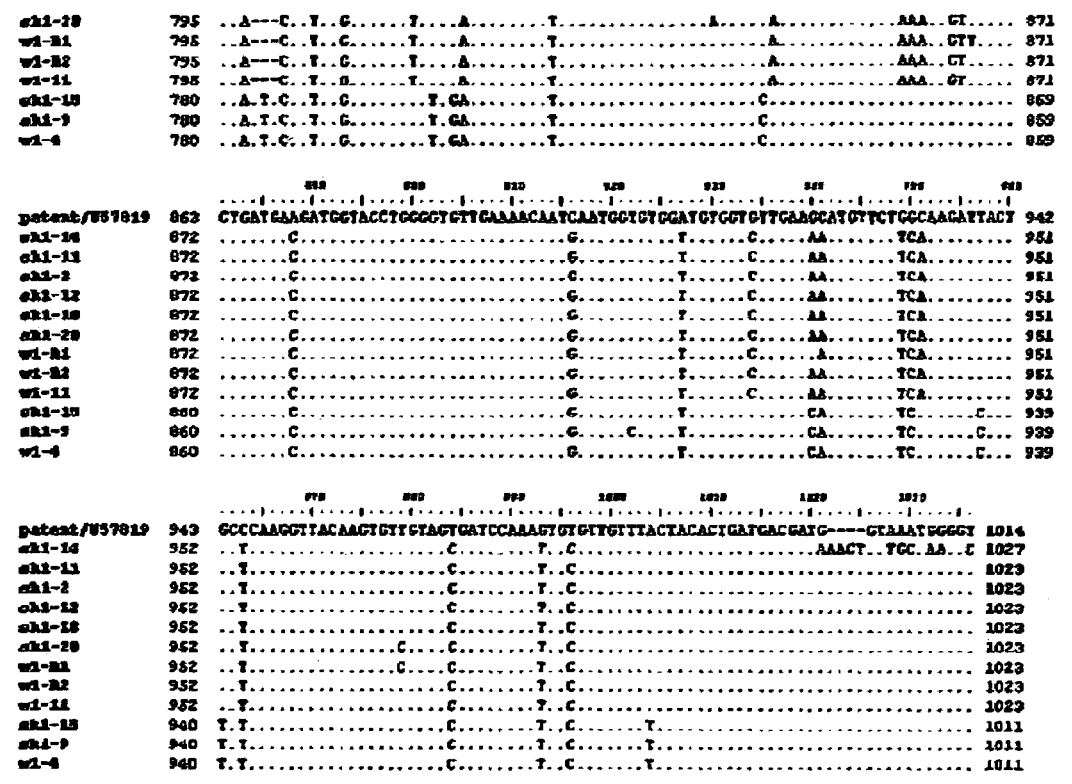

The purified PCR product was digested with 10 units of restriction enzymes EcoRI and BamHI and ligated into 50 ng of pGEX4T-1 or pMET α A, predigested with the same restriction enzymes. The transformation of *E. coli* with the resultant vector construct was carried out by utilizing CaCl₂ method described in Current Protocols in Molecular Cloning (Ausubel et al., 1994). Successfully transformed strains were cultured in Luria Broth medium containing 0.3% oat spelt xylan and screened via Congo Red dyeing method (Teather, R. M. and P. J. Wood, *Use of Congo red-polysaccharide interactions in enumeration and characterization of cellulolytic bacteria from the bovine rumen*. Appl Environ Microbiol, 1982. 43(4): p. 777-80). The transformation and screening of *P. methanolica* were carried out according to "A manual of methods for expression of recombinant proteins in *Pichia methanolica*, Invitrogen". The particulars of the adopted strains and vectors are explicitly listed in Table 3. The vector constructions are shown in FIG. 1 and FIG. 2. The detailed DNA sequences of the xylanase genes obtained in this way are listed in FIG. 3(*a*) and FIG. 4(*a*). The deduced amino acid sequences of the xylanases obtained in these ways are shown in FIG. 3(*b*) and FIG. 4(*b*).

TABLE 3

| Strains | Purposes | Genotype | Source |
|---|---|---|---|
| *Escherichia coli* (DH5α) | Vector construct and storage | F⁻ Φ80dlacZΔM15Δ(lacZYA-argF) U169, deoR, recA1, endA1, hsdR17 (rk⁻, mk⁺), gal⁻phoA, supE44 λ, ⁻thi⁻1, gyrA96, relA1 | Life technologies, GIBCOBRL |
| *E. coli* (BL21) | Expression | *E. coli* BF⁻, ompT, hsdS (rB⁻, mB⁻), gal, dcm | Amersham pharmacia biotech |
| pGEX4T-1 | Expression | Tac promoter, gst, Amp^r, lacI^q, pBR322 ori | Amersham pharmacia biotech |
| *Pichia methanolica* (PMAD11) | Expression | Ade2-11 | Invitrogen |
| pMETα A | Expression | AUG1 promoter, AUG1 transcription termination signal, ADE2, pMB1ori, Amp^r | Invitrogen |

Example 2

Large-Scale Expression of Recombinant Protein 2.1 Each colony of the successfully transformed *E. coli* strains was individually cultured in 150 ml of the LB medium containing 150 μg/ml ampicillin. Growth is monitored by WV absorbance until $OD_{600}$=0.6-0.9. Induction expression was performed with the non-hydrolyzable lactose analog isopropyl-β-D-1-thiogalactopyranoside (IPTG) for 16 hours. Cells were pelleted by centrifugation. The collected cells were then suspended in phosphate buffered saline (PBS, 140 mM NaCl, 2.7 mM KCl, 10 mM $Na_2HPO4$, 1.8 mM $KH_2PO_4$, pH7.4). The cells may be harvested and used directly or used after being ruptured by ultrasound, mechanical forces, enzymes, chemicals or high pressure. The resulting lysate may be directly used to exhibit xylanase activity or may be subject to further processing, such as centrifugation. If centrifugation was performed, the recombinant protein contained in the supernatant may be purified by Glutathion S-transferase (GST) affinity column. Detailed operation methods are shown in Manual for Operating GST Affinity Column (Amersham Pharmacia Biotech).

2.2 Each colony of the successfully transformed *P. methanolica* strains was individually cultured in 200 ml of YAPD (Yeast Extract/Agar/Peptone/Dextrose) medium for 16 hours. Cells were pelleted by centrifugation and suspended in BMMY medium. Subsequently, about 1 ml methanol per 24 hours was added into said medium until a concentration of 0.5% methanol was reached. A part of supernatant was taken at each of specific intervals to proceed with protein and enzyme analysis.

To scale up the expression of xylanase in *Pichia methanolica*, a Biosta® B fermentor (B. Braun biotech international) with a 5-L working volumes water-jacketed glass vessel was used for batch and fed-batch fermentation. The fermentation of *P. methanolica* included two phases: first a growth phase on dextrose followed by an induction phase on methanol. All fermentation began with a batch growth phase in 2.0 L of Buffer dextrose-complex medium (BMDY, 1% yeast extract, 2% peptone, 100 mM potassium phosphate, pH 6.0, 1.34% YNB, $4 \times 10^{-5}$% biotin, and 2% dextrose) at 30° C. Before inoculation, the pH was adjusted to 6.0 with concentrated ammonium hydroxide (28% (v/v)) and 2N sulfuric acid. An inoculum was grown in 250 ml baffled flask containing 50 ml BMDY medium and incubated at 30° C. for 16-18 hour at 250 rpm. Overnight culture was added to the fermentor to a final optical density of approximately 0.1 at 600 nm. The oxygen was supplied by using a constant flow of air (2.5 vvm) controlled by air pump (HIBLOW SPP-25GA), and the agitation was set to 800 rpm. The pH of the medium was automatically maintained at 6.0 with ammonium hydroxide and sulfuric acid.

After depletion of the dextrose, the cells were collected by centrifugation at 1,500 × g for 5 min at room temperature. Discard the supernatant, and the cell was re-suspended in 2 liter buffered methanol complex medium (BMMY 1% yeast extract, 2% peptone, 100 mM potassium phosphate, pH 6.0, 1.34% YNB, $4 \times 10^{-5}$% biotin, and 0.5% methanol), and was injected to fermentor. 0.5% Methanol was added every 4 hour. Samples were withdrawn every 12 hour for optical density measurement, viable cell measurement, xylanase activity assay, and determination of total soluble protein and gel electrophoresis analysis.

Example 3

Figure 7A:
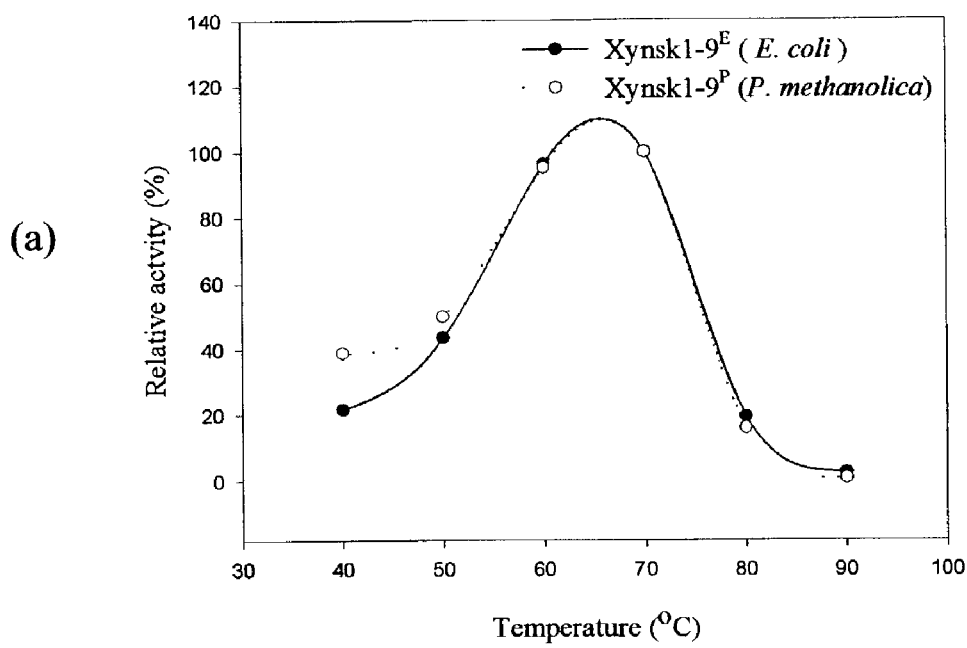
FIG. 7(*a*) shows optimal temperature of Xynsk1-9$^E$ and Xynsk1-9$^P$ separately expressed in *E. coli* (●) and *P. methanolica* (○).

Determination of the Optimal pH and Temperature of the Obtained Endo-β-1,4-xylanase Activity from the Culture Supernatant The recombinant proteins obtained after purification were diluted to $10^{-3}$-$10^{-4}$ mg/ml, in order to detect the activities of endo-β-1,4-xylanases. Activity detection is conducted by using dinitrosalicylic reagent (Miller, G. L., Use of dinitrosalicylic acid reagent for determination of reducing sugar, Anal. Chem. 31:426-428, 1959) to determine the amount of reducing carbohydrates and using xylose as a standard. Xylanase activities throughout the Examples were measured (Georis, J., et al., Sequence, overproduction and purification of the family 11 endo-beta-1,4-xylanase encoded by the xyl1 gene of *Streptomyces* sp. S38. Gene. 1999. 237(1): p. 123-33.) with the following modifications: pre-warming 0.36 ml substrate solution respectively at 40, 50, 60, 70, 80, and 90° C. for 5 min (water bath), adding 0.04 ml diluted- Enzyme solution, vertexing secs, and incubating respectively at 40, 50, 60, 70, 80, and 90° C. for 3 min. Subsequently, 0.5 ml DNS reagent was added to stop the reaction, and the reaction mixture was incubated at 100° C. for 10 min for colorization. Reducing sugar was determined by measuring the absorbance at 540 nm. The maximum activity is defined as 100%. The test results are shown in FIG. 7(a).

Figure 7B:
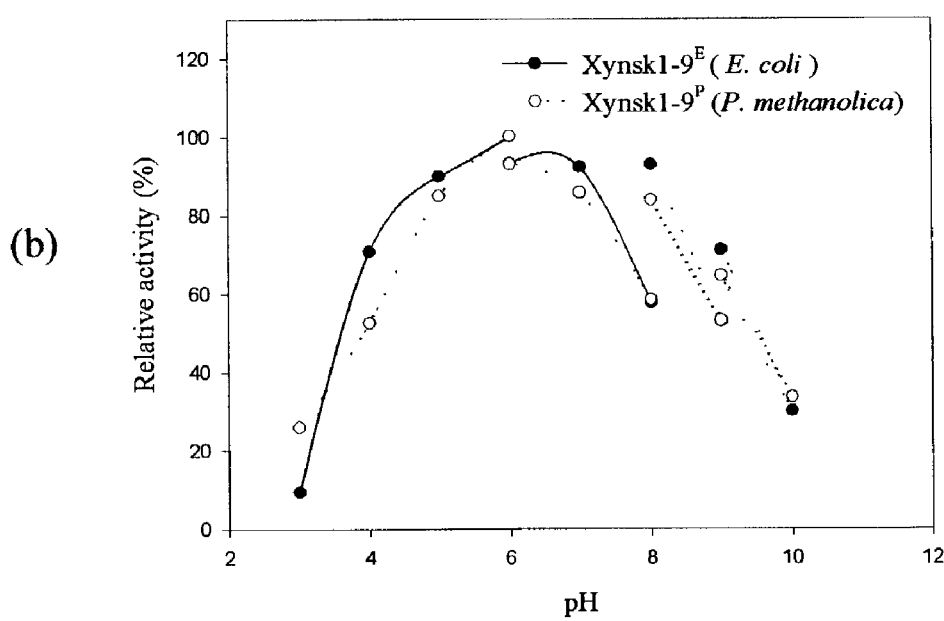

To determine the optimal pH for the obtained recombinant proteins, buffers used were 25 mM citrate buffer (pH3-6), phosphate buffer (pH6-8), Tris buffer (pH8-9), and Glycine buffer (pH9-10). Samples from the shake flask cultivation (culture supernatant) were diluted in each buffer and then incubated for 3 minutes. All units were corrected for substrate background reducing sugar groups in the pH or temperature range of the working buffer. Xylanase activity was measured at each pH at 70° C. The maximum activity is defined as 100%. The test results are shown in FIG. 7(b).

After DNA sequencing, it has been found that among those amplification products, 5 different sequences come from w1, and 9 different sequences come from sk1. Upon sequence comparison, it has been found that 4 sequences coming from w1 [namely, w1-A1 (SEQ ID No. 8), w1-A2 (SEQ ID No. 9), w1-4 (SEQ ID No. 14), and w1-11 (SEQ ID No. 10)], and 8 sequences coming from sk1 [namely, sk1-2 (SEQ ID No. 4), sk1-9 (SEQ ID No. 12), sk1-11 (SEQ ID No. 3), sk1-12 (SEQ ID No. 5), sk1-14 (SEQ ID No. 2), sk1-15 (SEQ ID No. 11), sk1-18 (SEQ ID No. 6), and sk1-20 (SEQ ID No. 7)] belong to endo-β-1,4-xylanase genes of rumen fungi (see FIG. 3(a)). Furthermore, in comparison with the prior arts, the sequence AAE25847 (SEQ ID No. 14) obtained from *N. patriciarum* and known from U.S. Pat. No. 5,948,667 and the sequence AAE12389 (SEQ ID No. 15) obtained from *Orpinomyces* sp. PC-2 and known from U.S. Pat. No. 5,824,533 are closest to the DNA and amino acid sequences of the present invention. The identity matrix of DNA sequence and that of amino acid sequence are respectively shown in Tables 4(a) and 4(b).

TABLE 4(a)

The identity matrix of DNA sequence

| | U66253 | sk1-14 | sk1-11 | sk1-2 | sk1-12 | sk1-18 | sk1-20 | w1-A1 | w1-A2 | w1-11 | sk1-15 | sk1-9 | w1-4 |
|---|---|---|---|---|---|---|---|---|---|---|---|---|---|
| U66253 | 1.000 | 0.844 | 0.847 | 0.846 | 0.848 | 0.845 | 0.847 | 0.847 | 0.848 | 0.847 | 0.852 | 0.852 | 0.853 |
| sk1-14 | — | 1.000 | 0.951 | 0.951 | 0.953 | 0.950 | 0.951 | 0.950 | 0.952 | 0.951 | 0.901 | 0.900 | 0.901 |
| sk1-11 | — | — | 1.000 | 0.995 | 0.998 | 0.994 | 0.996 | 0.994 | 0.997 | 1.000 | 0.943 | 0.942 | 0.943 |
| Sk1-2 | — | — | — | 1.000 | 0.997 | 0.993 | 0.995 | 0.993 | 0.996 | 0.995 | 0.942 | 0.941 | 0.942 |
| sk1-12 | — | — | — | — | 1.000 | 0.996 | 0.998 | 0.996 | 0.999 | 0.998 | 0.945 | 0.944 | 0.945 |
| sk1-18 | — | — | — | — | — | 1.000 | 0.994 | 0.992 | 0.995 | 0.994 | 0.941 | 0.940 | 0.941 |
| sk1-20 | — | — | — | — | — | — | 1.000 | 0.996 | 0.997 | 0.996 | 0.943 | 0.942 | 0.943 |
| w1-A1 | — | — | — | — | — | — | — | 1.000 | 0.995 | 0.994 | 0.942 | 0.941 | 0.942 |
| w1-A2 | — | — | — | — | — | — | — | — | 1.000 | 0.997 | 0.944 | 0.943 | 0.944 |
| w1-11 | — | — | — | — | — | — | — | — | — | 1.000 | 0.943 | 0.942 | 0.943 |
| sk1-15 | — | — | — | — | — | — | — | — | — | — | 1.000 | 0.997 | 0.998 |
| Sk1-9 | — | — | — | — | — | — | — | — | — | — | — | 1.000 | 0.999 |
| W1-4 | — | — | — | — | — | — | — | — | — | — | — | — | 1.000 |

TABLE 4(b)

The identity matrix of amino acid sequence.

| | AAE25847 | AAD04194 | SK1-14 | SK1-11 | SK1-2 | SK1-12 | SK1-18 | SK1-20 | W1-A1 | W1-A2 | W1-11 | SK1-15 | SK1-9 | W1-4 |
|---|---|---|---|---|---|---|---|---|---|---|---|---|---|---|
| AAE25847 | 1.000 | 0.201 | 0.198 | 0.200 | 0.203 | 0.203 | 0.203 | 0.203 | 0.203 | 0.203 | 0.200 | 0.200 | 0.200 | 0.200 |
| AAD04194 | — | 1.000 | 0.837 | 0.863 | 0.863 | 0.869 | 0.863 | 0.863 | 0.866 | 0.866 | 0.863 | 0.879 | 0.879 | 0.882 |
| SK1-14 | — | — | 1.000 | 0.957 | 0.957 | 0.963 | 0.957 | 0.957 | 0.960 | 0.957 | 0.887 | 0.887 | 0.890 |
| SK1-11 | — | — | — | 1.000 | 0.988 | 0.994 | 0.988 | 0.988 | 0.988 | 0.991 | 1.000 | 0.915 | 0.915 | 0.918 |
| SK1-2 | — | — | — | — | 1.000 | 0.994 | 0.988 | 0.988 | 0.988 | 0.991 | 0.988 | 0.915 | 0.915 | 0.918 |
| SK1-12 | — | — | — | — | — | 1.000 | 0.994 | 0.994 | 0.994 | 0.997 | 0.994 | 0.921 | 0.921 | 0.923 |
| SK1-18 | — | — | — | — | — | — | 1.000 | 0.988 | 0.988 | 0.991 | 0.988 | 0.915 | 0.915 | 0.918 |
| SK1-20 | — | — | — | — | — | — | — | 1.000 | 0.994 | 0.991 | 0.988 | 0.915 | 0.915 | 0.918 |
| W1-A1 | — | — | — | — | — | — | — | — | 1.000 | 0.991 | 0.988 | 0.918 | 0.918 | 0.921 |
| W1-A2 | — | — | — | — | — | — | — | — | — | 1.000 | 0.991 | 0.918 | 0.918 | 0.921 |
| W1-11 | — | — | — | — | — | — | — | — | — | — | 1.000 | 0.915 | 0.915 | 0.918 |
| SK1-15 | — | — | — | — | — | — | — | — | — | — | — | 1.000 | 0.994 | 0.997 |
| SK1-9 | — | — | — | — | — | — | — | — | — | — | — | — | 1.000 | 0.997 |
| W1-4 | — | — | — | — | — | — | — | — | — | — | — | — | — | 1.000 |

Example 4

Analysis of Nucleotide Sequencing and Amino Acid Sequencing

Using *Neocallimastix frontailis* (sk1) and *N. patriciarum* (w1) DNAs as templates for proceeding with PCR successfully obtained the amplification products of about 1000 bp.

Furthermore, sequence comparison shows that proteins SK1-6 (SEQ ID No. 32) and W1-6 (SEQ ID No. 33) belong to acetylxylan esterase of rumen fungi. Their amino acid sequences are most close to that of AAB69092 (SEQ ID No. 31) derived from *N. patriciarum*. The identity matrix of DNA sequence and that of amino acid sequence in this respect are respectively shown in FIGS. 4(a) and 4(b). The sequence identity is shown in Tables 5(a) and 5(b).

TABLE 5(a)

The identity matrix of DNA sequence

| Sequence | U66253 | sk1-6 | w1-6 |
|---|---|---|---|
| U66253 | 1.000 | 0.667 | 0.668 |
| sk1-6 | — | 1.000 | 0.998 |
| w1-6 | — | — | 1.000 |

TABLE 5(b)

The identity matrix of amino acid sequence

| Sequence | AAB69092 | SK1-6 | W1-6 |
|---|---|---|---|
| AAB69092 | 1.000 | 0.560 | 0.560 |
| SK1-6 | — | 1.000 | 0.996 |
| W1-6 | — | — | 1.000 |

It has been surprisingly found that the primers of the sequence aactgttgctaaggcccaatggggt (SEQ ID NO.: 34) or accccatttaccatcgtcatcagtg (SEQ ID NO.: 35) may successfully amplify not only endo-xylanases but also xylan esterase genes. This might be why said primers may successfully amplify the genes for encoding the xylan degradation enzymes.

Example 5

Activity Detection of Endo-β-1,4-xylanase

Figure 5:
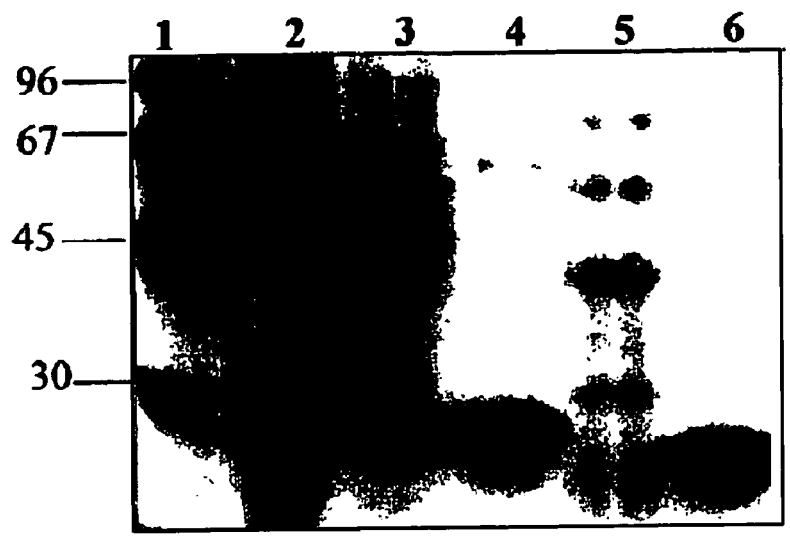
FIG. 5 shows the SDS-PAGE result of Xynsk1-9$^E$ expressed in *E. coli*, wherein lanes 1 and 5 refer to protein marker, lane 2 refers to cell lysate, lane 3 refers to sample flow, lane 4 refers to Xynsk1-9$^E$, and lane 6 refers to GST.

The recombinant proteins expressed by E. coli, after GST affinity column purification, were put into SDS-PAGE analysis (see FIG. 5). Eventually, a protein (named as Xynsk1-9$^E$, lane 4) with molecular mass of about 29 kDa has been isolated. Activity detection reveals that it possesses endo-β-1,4-xylanse activities.

Figure 6:
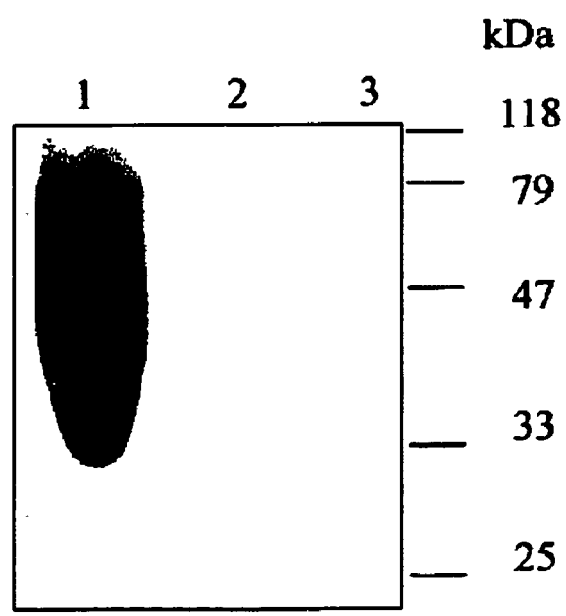
FIG. 6 shows the SDS-PAGE result of Xynsk1-9$^P$ expressed in *P. methanolica*, wherein lane 1 refers to culture supernatant after ultra-filtration, lane 2 refers to culture supernatant, and lane 3 refers to protein marker.

The culture supernatant of P. methanolica was collected and concentrated to one tenth of its original volume. The SDS-PAGE analysis of said supernatant as such and its concentrate shows a band from 33 to 118 kDa, and the relevant protein is named as Xynsk1-9$^P$ (lanes 1-2) (see FIG. 6).

Determination of the optimal temperature and pH as well as the substrate specificity reveals that Xynsk1-9$^E$ and Xynsk1-9$^P$ have the same tendency in these respects. Furthermore, the highest activity was observed at 70° C., pH 6 and when the substrate is 1% oat spelt xylan (see FIGS. 7(a) and 7(b)). In other words, Xynsk1-9$^E$ exhibits the highest specific activity 10371.04 U/mg protein after reacting in a substrate of 1% oat spelt xylan at 70° C. and pH 6 for 3 minutes (see Table 6).

TABLE 6

Substrates specificity of Xynsk1-9$^E$ and Xynsk1-9$^P$ expressed in E. coli and P. methanolica

| Substrates | E. coli U/ml | E. coli U/mg protein | P. methanolica[a] U/ml |
|---|---|---|---|
| 1% Oat spelts xylan (OSX) | 20742.07 | 10371.04 | 71686.7 |
| 1% Birch wood xylan (BWX) | 19043.32 | 9521.66 | 61685.65 |
| 0.5% Rye arabinoxylan (RAX) | 6665.42 | 3332.71 | 24908.56 |
| 0.5% Wheat arabinoxylan (WAX) | 5485.17 | 2742.59 | 20804.75 |
| 0.5% Carboxymethylcellulose (CMC) | N.D. | N.D. | N.D. |
| 0.2% Avicel | N.D. | N.D. | N.D. |

N.D. no detected,
[a]culture supernatant after ultra-filtration

What is claimed is:

1. An isolated polynucleotide comprising the nucleotide sequence of SEQ ID NO: 12.

2. A recombinant expression vector which comprises the polynucleotide of claim 1.

3. An isolated host cell transfected or transformed with the polynucleotide of claim 1.

4. The host cell according to claim 3, wherein the host cell is selected from a group consisting of *E. coli* and *Pichia methanolica*.

* * * * *

SEQUENCE LISTING

<160> NUMBER OF SEQ ID NOS: 33

<210> SEQ ID NO 1
<211> LENGTH: 1014
<212> TYPE: DNA
<213> ORGANISM: Orpinomyces sp. PC-2

<400> SEQUENCE: 1

```
accgttgcta aggcccaatg gggtggaaac ggtggtgcct ctgctggtca aagattaagc      60
gttggtggtg gtcaaaacca acataaaggt gttttgatg gcttcagtta tgaaatctgg     120
ttagataaca ccggtggtag tggttccatg acccttggta aagtgcaac cttcaaggct     180 gaatggagtg cagctgttaa ccgtggtaac ttccttgccc gtcgtggtct tgatttcggt     240
tctaccaaaa aggcaaccgc ttacgaatac atcggattgg attatgaagc aagttacaga     300
caaactgcca gcgcaagtgg taactcccgt ctttgtgtat acggctggtt ccaaaaccgt     360
ggagttcaag gcgtaccttt ggtagaatac tacatcattg aagattgggt tgactgggta     420
ccagatgcac aaggaaaaat ggtaaccatc gatggtgcac aatataagat tttccaaatg     480
gatcacactg gtccaactat caatggtggt aatgaaacct taagcaata cttcagtgtc     540
```

```
cgtcaacaaa agagaacttc tggtcatatt actgtatcag atcactttaa ggcatggtcc      600
aatcaaggtt ggggtattgg aaacctctat gaagttgcat tgaacgcaga aggttggcaa      660
agtagtggtg tcgctgacgt ccccaagttg gatgtctaca ccaccaaaca aggttctgct      720
cctcgtacta ccaccaccac tacccgtact actacccgta ctactacaaa aacacttcca      780
accactaata aaaatgttc tgccaagatt actgcccaag ttacaagtg ttgtagtgat        840 ccaaattgtg ttgtttacta cactgatgaa gatggtacct ggggtgttga aaacaatcaa      900
tggtgtggat gtggtgttga agcatgttct ggcaagatta ctgcccaagg ttacaagtgt      960
tgtagtgatc caaagtgtgt tgtttactac actgatgacg atggtaaatg gggt           1014

<210> SEQ ID NO 2
<211> LENGTH: 1027
<212> TYPE: DNA
<213> ORGANISM: Neocallimastix frontalis

<400> SEQUENCE: 2
actgttgcta aggcccaatg gggtggaggt gcttccgctg gtcaaaaatt atccgtcggt       60
ggtggtcaaa accaacataa gggtgtctcc gatggtttca gttatgaaat ctggttagat      120
aacaccggtg gtagcggttc tatgactctc ggtagtggtg caaccttcaa ggctgaatgg      180
aatgcagctg ttaaccgtgg taacttcctt gcccgtcgtg gccttgactt cggttctcaa      240
aagaaggcaa ccgactacag ctacatcgga ttggattata ctgcaactta cagacaaact      300
gccagtgcaa gtggtaactc ccgtctctgt gtatacggat ggttccaaaa ccgtggagtt      360
caaggtgttc ctttagtaga atactacatc attgaagatt gggttgactg gttccagat      420 gcacaaggaa aaatggtaac catcgatgga gctcaatata agatttttcca aatggatcac      480 actggtccaa ctatcaatgg tggtagtgaa accttttaagc aatacttcag tgtccgtcaa      540
caaaagagaa cttctggtca tattactgtc tcagatcact ttaaggaatg ggctaaacaa      600
ggttggggta ttggtaaccct ttatgaagtt gctttgaacg ccgaaggttg gcaaagtagt      660
ggtatagctg atgtcaccaa gttagatgtt tacacaaccc aaaaaggttc taatcctacc      720
accgccgctc gtactactcg tactactgcc cgtactactg cccgtactac tacccgtact      780
aagactcttc caaccaacaa taagtgttct tccaaaatta ctgctcaagg ttacaagtgt      840
tgtagtaatc caaattgtga aattgtctac actgatgacg atggtacctg gggtgttgaa      900
aacaatgaat ggtgtggttg tggtcttgaa aaatgttctt caaagattac tgctcaaggt      960
tacaagtgtt gtagcgatcc aaattgcgtt gtttactaca ctgatgacga taaactgttg     1020
ctaaggc                                                                1027

<210> SEQ ID NO 3
<211> LENGTH: 1023
<212> TYPE: DNA
<213> ORGANISM: Neocallimastix frontalis

<400> SEQUENCE: 3
actgttgcta aggcccaatg gggtggaggt gcttccgctg gtcaaaaatt atccgtcggt       60
ggtggtcaaa accaacataa gggtgtctcc gatggtttca gttatgaaat ctggttagat      120
aacaccggtg gtagcggttc tatgattctc ggtagtggtg caaccttcaa ggctgaatgg      180
aatgcagctg ttaaccgtgg taacttcctt gcccgtcgtg gtcttgactt cggttctcaa      240
aagaaggcaa ccgattacag ctacatcgga ttggattata ctgcaactta cagacaaact      300
```

```
gccagtgcaa gtggtaactc ccgtctctgt gtatacggat ggttccaaaa ccgtggagtt      360
caaggcgttc ctttagtaga atactacatc attgaagatt gggttgactg ggttccagat      420
gcacaaggaa aaatggtaac catcgatgga gctcaatata agattttcca aatggatcac      480
actggtccaa ctatcaatgg tggtagtgaa acctttaagc aatacttcag tgtccgtcaa      540
caaaagagaa cttctggtca tattactgtc tcagatcact ttaaggaatg ggctaaacat      600
ggttggggta ttggtaacct ttatgaagtt gctttgaacg ccgaaggttg gcaaagtagt      660
ggtatagctg atgtcaccaa gttagatgtt tacacaaccc aaaaaggttc taatcctacc      720
accgccgctc gtactactcg tactactgcc cgtactactg cccgtactac tacccgtact      780
aagactcttc caaccaacaa taagtgttct tccaaaatta ctgctcaagg ttacaagtgt      840
tgtagtaatc caaattgtga aattgtctac actgatgacg atggtacctg gggtgttgaa      900
aacaatgaat ggtgtggttg tggtcttgaa aaatgttctt caaagattac tgctcaaggt      960
tacaagtgtt gtagcgatcc aaattgcgtt gtttactaca ctgatgacga tggtaaatgg     1020
ggt                                                                   1023

<210> SEQ ID NO 4
<211> LENGTH: 1023
<212> TYPE: DNA
<213> ORGANISM: Neocallimastix frontalis

<400> SEQUENCE: 4
actgttgcta aggcccaatg gggtggaggt gcttccgctg gtcaaaaatt atccgtcggt       60
ggtggtcaaa accaatataa gggtgtctcc gatggtttca gttatgaaat ctggttagat      120
aacaccggtg gtagcggttc tatgactctc ggtagtggtg caaccttcaa ggctgaatgg      180
aatgcagctg ttaaccgtgg taacttcctt gcccgtcgtg gtcttgactt cggttctcaa      240
aagaaggcaa ccgattacag ctacatcgga ttggattata ctgcaactta cagacaaact      300
gccagtgcaa gtggtaactc ccgtctctgt gtatacggat ggttccaaaa ccgtggagtt      360
caaggcgttc ctttagtaga atactacatc attgaagatt gggttgactg ggttccagat      420
gcacaaggaa aaatggtaac catcgacgga gctcaatata agattatcca aatggatcac      480
actggtccaa ctatcaatgg tggtagtgaa acctttaagc aatacttcag tgtccgtcaa      540
caaaagagaa cttctggtca tattactgtc tcagatcact ttaaggaatg ggctaaacaa      600
ggttggggta ttggtaacct ttatgaagtt gctttgaacg ccgaaggttg gcaaagtagt      660
ggtatagctg atgtcaccaa gttagatgtt tacacaaccc aaaaaggttc taatcctacc      720
accgccgctc gtactactcg tactactgcc cgtactactg cccgtactac tacccgtact      780
aagactcttc caaccaacaa taagtgttct tccaaaatta ctgctcaagg ttacaagtgt      840
tgtagtaatc caaattgtga aattgtctac actgatgacg atggtacctg gggtgttgaa      900
aacaatgaat ggtgtggttg tggtcttgaa aaatgttctt caaagattac tgctcaaggt      960
tacaagtgtt gtagcgatcc aaattgcgtt gtttactaca ctgatgacga tggtaaatgg     1020
ggt                                                                   1023

<210> SEQ ID NO 5
<211> LENGTH: 1023
<212> TYPE: DNA
<213> ORGANISM: Neocallimastix frontalis

<400> SEQUENCE: 5
actgttgcta aggcccaatg gggtggaggt gcttccgctg gtcaaaaatt atccgtcggt       60
```

-continued

```
ggtggtcaaa accaacataa gggtgtctcc gatggtttca gttatgaaat ctggttagat        120
aacaccggtg gtagcggttc tatgactctc ggtagtggtg caaccttcaa ggctgaatgg        180
aatgcagctg ttaaccgtgg taacttcctt gcccgtcgtg gtcttgactt cggttctcaa        240
aagaaggcaa ccgattacag ctacatcgga ttggattata ctgcaactta cagacaaact        300
gccagtgcaa gtggtaactc ccgtctctgt gtatacggat ggttccaaaa ccgtggagtt        360
caaggcgttc ctttagtaga atactacatc attgaagatt gggttgactg ggttccagat        420
gcacaaggaa aaatggtaac catcgatgga gctcaatata agattttcca aatggatcac        480
actggtccaa ctatcaatgg tggtagtgaa acctttaagc aatacttcag tgtccgtcaa        540
caaaagagaa cttctggtca tattactgtc tcagatcact ttaaggaatg ggctaaacaa        600
ggttggggta ttggtaacct ttatgaagtt gctttgaacg ccgaaggttg gcaaagtagt        660
ggtatagctg atgtcaccaa gttagatgtt tacacaaccc aaaaaggttc taatcctacc        720
accgccgctc gtactactcg tactactgcc cgtactactg cccgtactac tacccgtact        780
aagactcttc caaccaacaa taagtgttct tccaaaatta ctgctcaagg ttacaagtgt        840
tgtagtaatc caaattgtga aattgtctac actgatgacg atggtacctg gggtgttgaa        900
aacaatgaat ggtgtggttg tggtcttgaa aaatgttctt caaagattac tgctcaaggt        960
tacaagtgtt gtagcgatcc aaattgcgtt gtttactaca ctgatgacga tggtaaatgg       1020
ggt                                                                    1023
```

<210> SEQ ID NO 6
<211> LENGTH: 1023
<212> TYPE: DNA
<213> ORGANISM: Neocallimastix frontalis

<400> SEQUENCE: 6

```
actgttgcta aggcccaatg gggtggaggt gcttccgctg gtcaaaaatt atccgtcggt         60
ggtggtcaaa accaacataa gggtgtctcc gatggtttca gttatgaaat ctggttagat        120
aacaccggtg gtagcggttc tatgactctc ggtagtggtg caaccttcaa ggctgaatgg        180
aatgcagctg ttaaccgtgg taacttcctt gcccgtcgtg gtctcgactt cggttctcaa        240
aagaaggcaa ccgattacag ctacatcgga ttggattata ctgtaactta cagacaaact        300
gccagtgcaa gtggtaactc ccgtctctgt gtatacggat ggttccaaaa ccgtggagtt        360
caaggcgttc ctctagtaga atactacatc attgaagatt gggttgactg ggttccagat        420
gcacaaggaa aaatggtaac catcgatgga gctcaatata agattttcca aatggatcac        480
actggtccaa ctatcaatgg tggtagtgaa acctttaagc aatacttcag tgtccgtcaa        540
caaaagagaa cttctggtca tattactgtc tcagatcact ttaaggaatg ggctaaacaa        600
ggttggggta ttggtaacct ttatgaagtt gctttgaacg ccgaaggttg gcaaagtagt        660
ggtatagctg atgtcaccaa gttagatgtt tacacaaccc aaaaaggttc taatcctacc        720
accgccgctc gtactactcg tactactgcc cgtactactg cccgtactac tacccgtact        780
aagactcttc caaccaacaa taagtgttct tccaaaatta ctgctcaagg ttacaagtgt        840
tgtagtaatc caaattgtga aattgtctac tctgatgacg atggtacctg gggtgttgaa        900
aacaatgaat ggtgtggttg tggtcttgaa aaatgttctt caaagattac tgctcaaggt        960
tacaagtgtt gtagcgatcc aaattgcgtt gtttactaca ctgatgacga tggtaaatgg       1020
ggt                                                                    1023
```

<210> SEQ ID NO 7
<211> LENGTH: 1023
<212> TYPE: DNA
<213> ORGANISM: Neocallimastix frontalis

<400> SEQUENCE: 7

| | | |
|---|---|---|
| actgttgcta aggcccaatg gggtggaggt gcttccgctg gtcaaaaatt atccgtcggt | 60 |
| ggtggtcaaa accaacataa gggtgtctcc gatggtttca gttatgaaat ctggttagat | 120 |
| aacaccggtg gtagcggttc tatgactctc ggtagtggtg caaccttcaa ggctgaatgg | 180 |
| aatgcagctg ttaaccgtgg taacttcctt gcccgtcgtg gtcttgactt cggttctcaa | 240 |
| aagaaggcaa ccgattacag ctacatcgga ttggattata ctgcaactta cagacaaact | 300 |
| gccagtgcaa gtggtaactc ccgtctctgt gtatacggat ggttccaaaa ccgtggagtt | 360 |
| caaggcgttc ctttagtaga atactacatc attgaagatt gggttgactg gttccagat | 420 |
| gcacaaggaa aaatggtaac catcgatgga gctcaatata agattttcca aatggatcac | 480 |
| actggtccaa ctatcaatgg tggtagtgaa acctttaagc aatacttcag tgtccgtcaa | 540 |
| caaaagagaa cttctggtca tattactgtc tcagatcact ttaaggaatg ggctaaacaa | 600 |
| ggttggggta ttggtaacct ttatgaagtt gctttgaacg ccgaaggttg gcaaagtagt | 660 |
| ggtatagctg atgtcaccaa gttagatgtt tacacaaccc aaaaaggttc taatcctacc | 720 |
| accgccgctc gtactactcg tactactgcc cgtactactg cccgtactac tcccgtact | 780 |
| aagactcttc caaccaacaa taagtgttct tccaaaatta ctgctcaagg ttacaagtgt | 840 |
| agtagtaatc caaattgtga aattgtctac actgatgacg atggtacctg gggtgttgaa | 900 |
| aacaatgaat ggtgtggttg tggtcttgaa aaatgttctt caaagattac tgctcaaggt | 960 |
| tacaagtgtc gtagcgatcc aaattgcgtt gtttactaca ctgatgacga tggtaaatgg | 1020 |
| ggt | 1023 |

<210> SEQ ID NO 8
<211> LENGTH: 1023
<212> TYPE: DNA
<213> ORGANISM: Neocallimastix patriciarum

<400> SEQUENCE: 8

| | | |
|---|---|---|
| actgttgcta aggcccaatg gggtggaggt gcttccgctg gtcaaaaatt atccgtcggt | 60 |
| ggtggtcaaa accaacataa gggtgtctcc gatggtttca gttatgaaat ctggttagat | 120 |
| aacaccggtg gtagcggttc tatgactctc ggtagtggtg caaccttcaa ggctgaatgg | 180 |
| aatgcagctg ttaaccgtgg taacttcctt gcccgtcgtg gtcttgactt cggttctcaa | 240 |
| aagaaggcaa ccgattacag ctacatcgga ttggattata ctgcaactta cagacaaact | 300 |
| gccagtgcaa gtggtaactc ccgcctctgt gtatacggat ggttccaaaa ccgtggagtt | 360 |
| caaggcgttc ctttagtaga atactacatc attgaagatt gggttgactg gttccagat | 420 |
| gcacaaggaa aaatggtaac catcgatgga gctcaatata agattttcca aatggatcac | 480 |
| actggtccaa ctatcaatgg tggtagtgaa acctttaagc aatacttcag tgtccgtcaa | 540 |
| caaaagagaa cttctggtca tattactgtc tcagatcact ttaaggaatg ggctaaacaa | 600 |
| ggttggggta ttggtaacct ttatgaagtt gctttgaacg ccgaaggttg gcaaagtagt | 660 |
| ggtatagctg atgtcaccaa gttagatgtt tacacaaccc aaaaaggttc taatcctacc | 720 |
| accgccgctc gtactactcg tactactgcc cgtactactg cccgtactac tcccgtact | 780 |
| aagactcttc caaccaacaa taagtgttct tccaaaatta ctgctcaagg ttacaagtgt | 840 |

```
tgtagtaatc caaattgtga aattgtttac actgatgacg atggtacctg gggtgttgaa      900
aacaatgaat ggtgtggttg tggtcttgaa gaatgttctt caaagattac tgctcaaggt      960
tacaagtgtc gtagcgatcc aaattgcgtt gtttactaca ctgatgacga tggtaaatgg     1020
ggt                                                                   1023

<210> SEQ ID NO 9
<211> LENGTH: 1023
<212> TYPE: DNA
<213> ORGANISM: Neocallimastix patriciarum

<400> SEQUENCE: 9
actgttgcta aggcccaatg gggtggaggt gcttccgctg gtcaaaaatt atccgtcggt       60
ggtggtcaaa accaacataa gggtgtctcc gatggtttca gttatgaaat ctggtcagat      120
aacaccggtg gtagcggttc tatgactctc ggtagtggtg caaccttcaa ggctgaatgg      180
aatgcagctg ttaaccgtgg taacttcctt gcccgtcgtg gtcttgactt cggttctcaa      240
aagaaggcaa ccgattacag ctacatcgga ttggattata ctgcaactta cagacaaact      300
gccagtgcaa gtggtaactc ccgtctctgt gtatacggat ggttccaaaa ccgtggagtt      360
caaggcgttc ctttagtaga atactacatc attgaagatt gggttgactg ggttccagat      420
gcacaaggaa aaatggtaac catcgatgga gctcaatata agattttcca aatggatcac      480
actggtccaa ctatcaatgg tggtagtgaa acctttaagc aatacttcag tgtccgtcaa      540
caaaagagaa cttctggtca tattactgtc tcagatcact ttaaggaatg ggctaaacaa      600
ggttggggta ttggtaacct ttatgaagtt gctttgaacg ccgaaggttg gcaaagtagt      660
ggtatagctg atgtcaccaa gttagatgtt tacacaaccc aaaaaggttc taatcctacc      720
accgccgctc gtactactcg tactactgcc cgtactactg cccgtactac tacccgtact      780
aagactcttc caaccaacaa taagtgttct tccaaaatta ctgctcaagg ttacaagtgt      840
tgtagtaatc caaattgtga aattgtctac actgatgacg atggtacctg gggtgttgaa      900
aacaatgaat ggtgtggttg tggtcttgaa aaatgttctt caaagattac tgctcaaggt      960
tacaagtgtt gtagcgatcc aaattgcgtt gtttactaca ctgatgacga tggtaaatgg     1020
ggt                                                                   1023

<210> SEQ ID NO 10
<211> LENGTH: 1023
<212> TYPE: DNA
<213> ORGANISM: Neocallimastix patriciarum

<400> SEQUENCE: 10
actgttgcta aggcccaatg gggtggaggt gcttccgctg gtcaaaaatt atccgtcggt       60
ggtggtcaaa accaacataa gggtgtctcc gatggtttca gttatgaaat ctggttagat      120
aacaccggtg gtagcggttc tatgattctc ggtagtggtg caaccttcaa ggctgaatgg      180
aatgcagctg ttaaccgtgg taacttcctt gcccgtcgtg gtcttgactt cggttctcaa      240
aagaaggcaa ccgattacag ctacatcgga ttggattata ctgcaactta cagacaaact      300
gccagtgcaa gtggtaactc ccgtctctgt gtatacggat ggttccaaaa ccgtggagtt      360
caaggcgttc ctttagtaga atactacatc attgaagatt gggttgactg ggttccagat      420
gcacaaggaa aaatggtaac catcgatgga gctcaatata agattttcca aatggatcac      480
actggtccaa ctatcaatgg tggtagtgaa acctttaagc aatacttcag tgtccgtcaa      540
```

-continued

```
caaaagagaa cttctggtca tattactgtc tcagatcact ttaaggaatg ggctaaacat      600
ggttggggta ttggtaacct ttatgaagtt gctttgaacg ccgaaggttg gcaaagtagt      660
ggtatagctg atgtcaccaa gttagatgtt tacacaaccc aaaaaggttc taatcctacc      720
accgccgctc gtactactcg tactactgcc cgtactactg cccgtactac tacccgtact      780
aagactcttc caaccaacaa taagtgttct tccaaaatta ctgctcaagg ttacaagtgt      840
tgtagtaatc caaattgtga aattgtctac actgatgaca atggtacctg gggtgttgaa      900
aacaatgaat ggtgtggttg tggtcttgaa aaatgttctt caaagattac tgctcaaggt      960
tacaagtgtt gtagcgatcc aaattgcgtt gtttactaca ctgatgacga tggtaaatgg     1020
ggt                                                                   1023
```

<210> SEQ ID NO 11
<211> LENGTH: 1011
<212> TYPE: DNA
<213> ORGANISM: Neocallimastix frontalis

<400> SEQUENCE: 11

```
actgttgcta aggcccaatg gggtggaggt gcttccgctg gtcaaaaatt atccgtcggt       60
ggtggtcaaa accaacataa gggtgtctcc gatggtttca gttatgaaat ctggttagat      120
aacaccggtg gtagcggttc tatgactctc ggtagtggtg caaccttcaa ggctgaatgg      180
aatgcagctg ttaaccgtgg taacttcctt gcccgtcgtg gtcttgactt cggttctcaa      240
aagaaggcag ccgattacag ctacatcgga ttggattata ctgcaactta cagacaaact      300
gccagtgcaa gtggtaactc ccgtctctgt gtatacggat ggttccaaaa ccgtggagtt      360
caaggcgttc ctttagtaga atactacatc attgaagatt gggttgactg ggttccagat      420
gcacaaggaa aaatggtaac catcgatgga gctcaatata agattttcca aatggatcac      480
actggtccaa ctatcaatgg tggtagtgaa acctttaagc aatacttcag tgtccgtcaa      540
caaaagagaa cttctggtca tattactgtc tcagatcact ttaaggaatg ggctaaacaa      600
ggttggggta ttggtaacct ttatgaagtt gctttgaacg ccgaaggttg gcaaagtagt      660
ggtgttgctg atgtcacctt attagatgtt tacacaactc caaagggttc tagtccagcc      720
acctctgccg ctcctcgtac tactacccgt actactactc gtaccaagtc tcttccaacc      780
aattacaata agtgttctgc tagaattact gctcaaggtt acaagtgttg tagcgatcca      840
aattgtgttg tttactacac tgatgacgat ggtacctggg gtgttgaaaa caatgaatgg      900
tgtggttgtg gtgttgaaca atgttcttcc aagatcactt ctcaaggtta caagtgttgt      960
agcgatccaa attgcgttgt tttctacact gatgacgatg gtaaatgggg t              1011
```

<210> SEQ ID NO 12
<211> LENGTH: 1011
<212> TYPE: DNA
<213> ORGANISM: Neocallimastix frontalis

<400> SEQUENCE: 12

```
actgttgcta aggcccaatg gggtggaggt gcttccgctg gtcaaaaatt atccgtcggt       60
ggtggtcaaa accaacataa gggtgtctcc gatggtttca gttatgaaat ctggttagat      120
aacaccggtg gtagcggttc tatgactctc ggtagtggtg caaccttcaa ggctgaatgg      180
aatgcagctg ttaaccgtgg taacttcctt gcccgtcgtg gtcttgactt cggttctcaa      240
aagaaggcaa ccgattacag ctacatcgga ttggattata ctgcaactta cagacaaact      300
gccagtgcaa gtggtaactc ccgtctctgt gtatacggat ggttccaaaa ccgtggagtt      360
```

```
caaggcgttc ctttagtaga atactacatc attgaagatt gggttgactg ggttccagat    420
gcacaaggaa aaatggtaac catcgatgga gctcaatata agattttcca aatggatcac    480
actggtccaa ctatcaatgg tggtagtgaa acctttaagc aatacttcag tgtccgtcaa    540
caaaagagaa cttctggtca tattactgtc tcagatcact ttaaggaatg ggctaagcaa    600
ggttggggta ttggtaacct ttatgaagtt gctttgaacg ccgaaggttg gcaaagtagt    660
ggtgttgctg atgtcacctt attagatgtt tacacaactc caaagggttc tagtccagcc    720
acctctgccg ctcctcgtac tactacccgt actactactc gtaccaagtc tcttccaacc    780
aattacaata gtgttctgc tagaattact gctcaaggtt acaagtgttg tagcgatcca    840
aattgtgttg tttactacac tgatgacgat ggtacctggg gtgttgaaaa caatgaatgg    900
cgtggttgtg gtgttgaaca atgttcttcc aagatcactt ctcaaggtta caagtgttgt    960
agcgatccaa attgcgttgt tttctacact gatgacgatg gtaaatgggg t            1011
```

<210> SEQ ID NO 13
<211> LENGTH: 1011
<212> TYPE: DNA
<213> ORGANISM: Neocallimastix patriciarum

<400> SEQUENCE: 13

```
actgttgcta aggcccaatg gggtggaggt gcttccgctg gtcaaaaatt atccgtcggt     60
ggtggtcaaa accaacataa gggtgtctcc gatggtttca gttatgaaat ctggttagat    120
aacaccggtg gtagcggttc tatgactctc ggtagtggtc aaccttcaa ggctgaatgg     180 aatgcagctg ttaaccgtgg taacttcctt gcccgtcgtg gtcttgactt cggttctcaa    240
aagaaggcaa ccgattacag ctacatcgga ttggattata ctgcaactta cagacaaact    300
gccagtgcaa gtggtaactc ccgtctctgt gtatacggat ggttccaaaa ccgtggagtt    360
caaggcgttc ctttagtaga atactacatc attgaagatt gggttgactg ggttccagat    420
gcacaaggaa aaatggtaac catcgatgga gctcaatata agattttcca aatggatcac    480
actggtccaa ctatcaatgg tggtagtgaa acctttaagc aatacttcag tgtccgtcaa    540
caaaagagaa cttctggtca tattactgtc tcagatcact ttaaggaatg ggctaagcaa    600
ggttggggta ttggtaacct ttatgaagtt gctttgaacg ccgaaggttg gcaaagtagt    660
ggtgttgctg atgtcacctt attagatgtt tacacaactc caaagggttc tagtccagcc    720
acctctgccg ctcctcgtac tactacccgt actactactc gtaccaagtc tcttccaacc    780
aattacaata gtgttctgc tagaattact gctcaaggtt acaagtgttg tagcgatcca    840
aattgtgttg tttactacac tgatgacgat ggtacctggg gtgttgaaaa caatgaatgg    900
tgtggttgtg gtgttgaaca atgttcttcc aagatcactt ctcaaggtta caagtgttgt    960
agcgatccaa attgcgttgt tttctacact gatgacgatg gtaaatgggg t            1011
```

<210> SEQ ID NO 14
<211> LENGTH: 448
<212> TYPE: PRT
<213> ORGANISM: Neocallimastix patriciarum

<400> SEQUENCE: 14

```
Thr Leu Ala Gln Ser Phe Cys Ser Ser Ala Ser His Ser Gly Gln Ser
1               5                   10                  15

Val Lys Glu Thr Gly Asn Lys Val Gly Thr Ile Gly Gly Val Gly Tyr
            20                  25                  30
```

```
Glu Leu Trp Ala Asp Ser Gly Asn Asn Ser Ala Thr Phe Tyr Ser Asp
         35                  40                  45

Gly Ser Phe Ser Cys Thr Phe Gln Asn Ala Gly Asp Tyr Leu Cys Arg
         50                  55                  60

Ser Gly Leu Ser Phe Asp Ser Thr Lys Thr Pro Ser Gln Ile Gly Arg
 65                  70                  75                  80

Met Lys Ala Asp Phe Lys Leu Val Lys Thr Lys Tyr Phe Gln Cys Trp
                 85                  90                  95

Leu Phe Leu Cys Trp Cys Leu Arg Trp Thr Arg Ser Pro Leu Val Gly
                100                 105                 110

Ile Leu His Val Asp Asn Trp Leu Ser Pro Ser Pro Gly Asp Trp
        115                 120                 125

Val Gly Asn Lys Lys His Gly Ser Phe Thr Ile Asp Gly Ala Gln Tyr
        130                 135                 140

Thr Val Tyr Glu Asn Thr Arg Thr Gly Pro Ser Ile Asp Gly Asn Thr
145                 150                 155                 160

Thr Phe Lys Gln Tyr Phe Ser Ile Arg Gln Gln Ala Arg Asp Cys Gly
                165                 170                 175

Thr Ile Asp Ile Ser Ala His Phe Asp Gln Trp Glu Lys Leu Gly Met
            180                 185                 190

Thr Met Gly Lys Leu His Glu Ala Lys Val Leu Gly Glu Ala Gly Asn
        195                 200                 205

Gly Asn Gly Gly Val Ser Gly Thr Ala Asp Phe Pro Tyr Ala Lys Val
        210                 215                 220

Tyr Ile Gly Asp Gly Asn Gly Gly Ala Ser Pro Ala Pro Ala Gly
225                 230                 235                 240

Gly Ala Pro Ala Gly Gly Ala Pro Ala Gly Asn Asp Gln Pro Gln Gly
                245                 250                 255

Pro Gln Gly Gln Gln Pro Pro Gln Gly Gln Gln Pro Pro Gln Gly Gln
                260                 265                 270

Gln Pro Pro Gln Gly Gln Gln Pro Pro Gln Gly Gln Gln Pro Pro Gln
        275                 280                 285

Gly Asn Asp Gln Gln Gly Gln Pro Pro Gln Gly Gln Gln Pro Pro
290                 295                 300

Gln Gly Asn Asp Gln Gln Gly Gln Gln Pro Pro Gln Pro Gln Gly
305                 310                 315                 320

Pro Gln Gly Gly Asn Pro Gly Gly Ser Asp Phe Asn Asn Trp Asn Gln
                325                 330                 335

Gly Gly Ser Pro Trp Gly Gly Asn Gln Gly Gly Ser Pro Trp Gly Gly
            340                 345                 350

Asn Gln Gly Gly Asn Pro Trp Gly Gly Asn Gln Gly Gly Ser Pro Trp
        355                 360                 365

Gly Gly Asn Gln Gly Gly Ser Pro Trp Gly Gly Asn Gln Gly Gly
370                 375                 380

Asn Pro Trp Gly Gly Asn Gln Gly Gly Ser Pro Trp Gly Gly Asn Gln
385                 390                 395                 400

Gly Gly Asn Pro Trp Gly Gly Asn Gln Trp Gly Ala Pro Gln Asn Ala
            405                 410                 415

Ala Ala Pro Gln Ser Ala Ala Pro Gln Asn Ala Ser Asp Gly Gly
        420                 425                 430

Asn Cys Ala Ser Leu Trp Gly Gln Cys Gly Gly Gln Gly Tyr Asn Gly
        435                 440                 445
```

<210> SEQ ID NO 15
<211> LENGTH: 338
<212> TYPE: PRT
<213> ORGANISM: Orpinomyces sp. PC-2

<400> SEQUENCE: 15

Thr Val Ala Lys Ala Gln Trp Gly Gly Asn Gly Ala Ser Ala Gly
1               5                   10                  15

Gln Arg Leu Ser Val Gly Gly Gln Asn Gln His Lys Gly Val Phe
            20                  25                  30

Asp Gly Phe Ser Tyr Glu Ile Trp Leu Asp Asn Thr Gly Ser Gly
            35                  40                  45

Ser Met Thr Leu Gly Lys Gly Ala Thr Phe Lys Ala Glu Trp Ser Ala
50                  55                  60

Ala Val Asn Arg Gly Asn Phe Leu Ala Arg Arg Gly Leu Asp Phe Gly
65                  70                  75                  80

Ser Thr Lys Lys Ala Thr Ala Tyr Glu Tyr Ile Gly Leu Asp Tyr Glu
                85                  90                  95

Ala Ser Tyr Arg Gln Thr Ala Ser Ala Ser Gly Asn Ser Arg Leu Cys
            100                 105                 110

Val Tyr Gly Trp Phe Gln Asn Arg Gly Val Gln Gly Val Pro Leu Val
        115                 120                 125

Glu Tyr Tyr Ile Ile Glu Asp Trp Val Asp Trp Val Pro Asp Ala Gln
130                 135                 140

Gly Lys Met Val Thr Ile Asp Gly Ala Gln Tyr Lys Ile Phe Gln Met
145                 150                 155                 160

Asp His Thr Gly Pro Thr Ile Asn Gly Gly Asn Glu Thr Phe Lys Gln
                165                 170                 175

Tyr Phe Ser Val Arg Gln Gln Lys Arg Thr Ser Gly His Ile Thr Val
            180                 185                 190

Ser Asp His Phe Lys Ala Trp Ser Asn Gln Gly Trp Gly Ile Gly Asn
        195                 200                 205

Leu Tyr Glu Val Ala Leu Asn Ala Glu Gly Trp Gln Ser Ser Gly Val
    210                 215                 220

Ala Asp Val Pro Lys Leu Asp Val Tyr Thr Thr Lys Gln Gly Ser Ala
225                 230                 235                 240

Pro Arg Thr Thr Thr Thr Thr Arg Thr Thr Thr Arg Thr Thr Thr
                245                 250                 255

Lys Thr Leu Pro Thr Thr Asn Lys Lys Cys Ser Ala Lys Ile Thr Ala
                260                 265                 270

Gln Gly Tyr Lys Cys Cys Ser Asp Pro Asn Cys Val Val Tyr Tyr Thr
            275                 280                 285

Asp Glu Asp Gly Thr Trp Gly Val Glu Asn Asn Gln Trp Cys Gly Cys
        290                 295                 300

Gly Val Glu Ala Cys Ser Gly Lys Ile Thr Ala Gln Gly Tyr Lys Cys
305                 310                 315                 320

Cys Ser Asp Pro Lys Cys Val Val Tyr Tyr Thr Asp Asp Gly Lys
                325                 330                 335

Trp Gly

<210> SEQ ID NO 16
<211> LENGTH: 354
<212> TYPE: PRT
<213> ORGANISM: Neocallimastix frontalis

<400> SEQUENCE: 16

```
Thr Val Ala Lys Ala Gln Trp Gly Gly Gly Ala Ser Ala Gly Gln Lys
1               5                   10                  15

Leu Ser Val Gly Gly Gly Gln Asn Gln His Lys Gly Val Ser Asp Gly
            20                  25                  30

Phe Ser Tyr Glu Ile Trp Leu Asp Asn Thr Gly Ser Gly Ser Met
        35                  40                  45

Thr Leu Gly Ser Gly Ala Thr Phe Lys Ala Glu Trp Asn Ala Ala Val
    50                  55                  60

Asn Arg Gly Asn Phe Leu Ala Arg Arg Gly Leu Asp Phe Gly Ser Gln
65                  70                  75                  80

Lys Lys Ala Thr Asp Tyr Ser Tyr Ile Gly Leu Asp Tyr Thr Ala Thr
            85                  90                  95

Tyr Arg Gln Thr Ala Ser Ala Ser Gly Asn Ser Arg Leu Cys Val Tyr
            100                 105                 110

Gly Trp Phe Gln Asn Arg Gly Val Gln Gly Val Pro Leu Val Glu Tyr
            115                 120                 125

Tyr Ile Ile Glu Asp Trp Val Asp Trp Val Pro Asp Ala Gln Gly Lys
130                 135                 140

Met Val Thr Ile Asp Gly Ala Gln Tyr Lys Ile Phe Gln Met Asp His
145                 150                 155                 160

Thr Gly Pro Thr Ile Asn Gly Gly Ser Glu Thr Phe Lys Gln Tyr Phe
            165                 170                 175

Ser Val Arg Gln Gln Lys Arg Thr Ser Gly His Ile Thr Val Ser Asp
            180                 185                 190

His Phe Lys Glu Trp Ala Lys Gln Gly Trp Gly Ile Gly Asn Leu Tyr
            195                 200                 205

Glu Val Ala Leu Asn Ala Glu Gly Trp Gln Ser Ser Gly Ile Ala Asp
            210                 215                 220

Val Thr Lys Leu Asp Val Tyr Thr Thr Gln Lys Gly Ser Asn Pro Thr
225                 230                 235                 240

Thr Ala Ala Arg Thr Thr Arg Thr Thr Ala Arg Thr Thr Ala Arg Thr
            245                 250                 255

Thr Thr Arg Thr Lys Thr Leu Pro Thr Asn Asn Lys Cys Ser Ser Lys
            260                 265                 270

Ile Thr Ala Gln Gly Tyr Lys Cys Cys Ser Asn Pro Asn Cys Glu Ile
            275                 280                 285

Val Tyr Thr Asp Asp Asp Gly Thr Trp Gly Val Glu Asn Asn Glu Trp
            290                 295                 300

Cys Gly Cys Gly Leu Glu Lys Cys Ser Ser Lys Ile Thr Ala Gln Gly
305                 310                 315                 320

Tyr Lys Cys Cys Ser Asp Pro Asn Cys Val Val Tyr Tyr Thr Asp Asp
            325                 330                 335

Asp Lys Leu Leu Leu Arg Pro Asn Gly Val Thr Asp Asp Gly Lys
            340                 345                 350

Trp Gly
```

<210> SEQ ID NO 17
<211> LENGTH: 341
<212> TYPE: PRT
<213> ORGANISM: Neocallimastix frontalis

<400> SEQUENCE: 17

```
Thr Val Ala Lys Ala Gln Trp Gly Gly Gly Ala Ser Ala Gly Gln Lys
1               5                   10                  15
```

```
Leu Ser Val Gly Gly Gly Gln Asn Gln His Lys Gly Val Ser Asp Gly
            20                  25                  30

Phe Ser Tyr Glu Ile Trp Leu Asp Asn Thr Gly Gly Ser Gly Ser Met
        35                  40                  45

Ile Leu Gly Ser Gly Ala Thr Phe Lys Ala Glu Trp Asn Ala Ala Val
    50                  55                  60

Asn Arg Gly Asn Phe Leu Ala Arg Arg Gly Leu Asp Phe Gly Ser Gln
65                  70                  75                  80

Lys Lys Ala Thr Asp Tyr Ser Tyr Ile Gly Leu Asp Tyr Thr Ala Thr
                85                  90                  95

Tyr Arg Gln Thr Ala Ser Ala Ser Gly Asn Ser Arg Leu Cys Val Tyr
            100                 105                 110

Gly Trp Phe Gln Asn Arg Gly Val Gln Gly Val Pro Leu Val Glu Tyr
        115                 120                 125

Tyr Ile Ile Glu Asp Trp Val Asp Trp Val Pro Asp Ala Gln Gly Lys
    130                 135                 140

Met Val Thr Ile Asp Gly Ala Gln Tyr Lys Ile Phe Gln Met Asp His
145                 150                 155                 160

Thr Gly Pro Thr Ile Asn Gly Gly Ser Glu Thr Phe Lys Gln Tyr Phe
                165                 170                 175

Ser Val Arg Gln Gln Lys Arg Thr Ser Gly His Ile Thr Val Ser Asp
            180                 185                 190

His Phe Lys Glu Trp Ala Lys His Gly Trp Gly Ile Gly Asn Leu Tyr
        195                 200                 205

Glu Val Ala Leu Asn Ala Glu Gly Trp Gln Ser Ser Gly Ile Ala Asp
    210                 215                 220

Val Thr Lys Leu Asp Val Tyr Thr Thr Gln Lys Gly Ser Asn Pro Thr
225                 230                 235                 240

Thr Ala Ala Arg Thr Thr Arg Thr Thr Ala Arg Thr Thr Ala Arg Thr
                245                 250                 255

Thr Thr Arg Thr Lys Thr Leu Pro Thr Asn Asn Lys Cys Ser Ser Lys
            260                 265                 270

Ile Thr Ala Gln Gly Tyr Lys Cys Cys Ser Asn Pro Asn Cys Glu Ile
        275                 280                 285

Val Tyr Thr Asp Asp Asp Gly Thr Trp Gly Val Glu Asn Asn Glu Trp
    290                 295                 300

Cys Gly Cys Gly Leu Glu Lys Cys Ser Ser Lys Ile Thr Ala Gln Gly
305                 310                 315                 320

Tyr Lys Cys Cys Ser Asp Pro Asn Cys Val Val Tyr Tyr Thr Asp Asp
                325                 330                 335

Asp Gly Lys Trp Gly
            340

<210> SEQ ID NO 18
<211> LENGTH: 341
<212> TYPE: PRT
<213> ORGANISM: Neocallimastix frontalis

<400> SEQUENCE: 18

Thr Val Ala Lys Ala Gln Trp Gly Gly Ala Ser Ala Gly Gln Lys
1               5                   10                  15

Leu Ser Val Gly Gly Gly Gln Asn Gln Tyr Lys Gly Val Ser Asp Gly
            20                  25                  30

Phe Ser Tyr Glu Ile Trp Leu Asp Asn Thr Gly Gly Ser Gly Ser Met
```

```
                35                  40                  45
Thr Leu Gly Ser Gly Ala Thr Phe Lys Ala Glu Trp Asn Ala Ala Val
         50                  55                  60

Asn Arg Gly Asn Phe Leu Ala Arg Arg Gly Leu Asp Phe Gly Ser Gln
 65                  70                  75                  80

Lys Lys Ala Thr Asp Tyr Ser Tyr Ile Gly Leu Asp Tyr Thr Ala Thr
                 85                  90                  95

Tyr Arg Gln Thr Ala Ser Ala Ser Gly Asn Ser Arg Leu Cys Val Tyr
            100                 105                 110

Gly Trp Phe Gln Asn Arg Gly Val Gln Gly Val Pro Leu Val Glu Tyr
        115                 120                 125

Tyr Ile Ile Glu Asp Trp Val Asp Trp Val Pro Asp Ala Gln Gly Lys
    130                 135                 140

Met Val Thr Ile Asp Gly Ala Gln Tyr Lys Ile Ile Gln Met Asp His
145                 150                 155                 160

Thr Gly Pro Thr Ile Asn Gly Gly Ser Glu Thr Phe Lys Gln Tyr Phe
                165                 170                 175

Ser Val Arg Gln Gln Lys Arg Thr Ser Gly His Ile Thr Val Ser Asp
            180                 185                 190

His Phe Lys Glu Trp Ala Lys Gln Gly Trp Gly Ile Gly Asn Leu Tyr
        195                 200                 205

Glu Val Ala Leu Asn Ala Glu Gly Trp Gln Ser Ser Gly Ile Ala Asp
    210                 215                 220

Val Thr Lys Leu Asp Val Tyr Thr Thr Gln Lys Gly Ser Asn Pro Thr
225                 230                 235                 240

Thr Ala Ala Arg Thr Thr Arg Thr Thr Ala Arg Thr Thr Ala Arg Thr
                245                 250                 255

Thr Thr Arg Thr Lys Thr Leu Pro Thr Asn Asn Lys Cys Ser Ser Lys
            260                 265                 270

Ile Thr Ala Gln Gly Tyr Lys Cys Cys Ser Asn Pro Asn Cys Glu Ile
        275                 280                 285

Val Tyr Thr Asp Asp Gly Thr Trp Gly Val Glu Asn Asn Glu Trp
    290                 295                 300

Cys Gly Cys Gly Leu Glu Lys Cys Ser Ser Lys Ile Thr Ala Gln Gly
305                 310                 315                 320

Tyr Lys Cys Cys Ser Asp Pro Asn Cys Val Val Tyr Tyr Thr Asp Asp
                325                 330                 335

Asp Gly Lys Trp Gly
            340

<210> SEQ ID NO 19
<211> LENGTH: 341
<212> TYPE: PRT
<213> ORGANISM: Neocallimastix frontalis

<400> SEQUENCE: 19

Thr Val Ala Lys Ala Gln Trp Gly Gly Gly Ala Ser Ala Gly Gln Lys
 1               5                  10                  15

Leu Ser Val Gly Gly Gln Asn Gln His Lys Gly Val Ser Asp Gly
             20                  25                  30

Phe Ser Tyr Glu Ile Trp Leu Asp Asn Thr Gly Gly Ser Gly Ser Met
         35                  40                  45

Thr Leu Gly Ser Gly Ala Thr Phe Lys Ala Glu Trp Asn Ala Ala Val
     50                  55                  60
```

```
Asn Arg Gly Asn Phe Leu Ala Arg Arg Gly Leu Asp Phe Gly Ser Gln
 65                  70                  75                  80

Lys Lys Ala Thr Asp Tyr Ser Tyr Ile Gly Leu Asp Tyr Thr Ala Thr
                 85                  90                  95

Tyr Arg Gln Thr Ala Ser Ala Ser Gly Asn Ser Arg Leu Cys Val Tyr
            100                 105                 110

Gly Trp Phe Gln Asn Arg Gly Val Gln Gly Val Pro Leu Val Glu Tyr
        115                 120                 125

Tyr Ile Ile Glu Asp Trp Val Asp Trp Val Pro Asp Ala Gln Gly Lys
130                 135                 140

Met Val Thr Ile Asp Gly Ala Gln Tyr Lys Ile Phe Gln Met Asp His
145                 150                 155                 160

Thr Gly Pro Thr Ile Asn Gly Gly Ser Glu Thr Phe Lys Gln Tyr Phe
                165                 170                 175

Ser Val Arg Gln Gln Lys Arg Thr Ser Gly His Ile Thr Val Ser Asp
            180                 185                 190

His Phe Lys Glu Trp Ala Lys Gln Gly Trp Gly Ile Gly Asn Leu Tyr
        195                 200                 205

Glu Val Ala Leu Asn Ala Glu Gly Trp Gln Ser Ser Gly Ile Ala Asp
    210                 215                 220

Val Thr Lys Leu Asp Val Tyr Thr Thr Gln Lys Gly Ser Asn Pro Thr
225                 230                 235                 240

Thr Ala Ala Arg Thr Thr Arg Thr Thr Ala Arg Thr Thr Ala Arg Thr
                245                 250                 255

Thr Thr Arg Thr Lys Thr Leu Pro Thr Asn Asn Lys Cys Ser Ser Lys
            260                 265                 270

Ile Thr Ala Gln Gly Tyr Lys Cys Cys Ser Asn Pro Asn Cys Glu Ile
        275                 280                 285

Val Tyr Thr Asp Asp Asp Gly Thr Trp Gly Val Glu Asn Asn Glu Trp
    290                 295                 300

Cys Gly Cys Gly Leu Glu Lys Cys Ser Ser Lys Ile Thr Ala Gln Gly
305                 310                 315                 320

Tyr Lys Cys Cys Ser Asp Pro Asn Cys Val Val Tyr Tyr Thr Asp Asp
                325                 330                 335

Asp Gly Lys Trp Gly
            340

<210> SEQ ID NO 20
<211> LENGTH: 341
<212> TYPE: PRT
<213> ORGANISM: Neocallimastix frontalis

<400> SEQUENCE: 20

Thr Val Ala Lys Ala Gln Trp Gly Gly Ala Ser Ala Gly Gln Lys
1                5                  10                  15

Leu Ser Val Gly Gly Gln Asn Gln His Lys Gly Val Ser Asp Gly
                20                  25                  30

Phe Ser Tyr Glu Ile Trp Leu Asp Asn Thr Gly Gly Ser Gly Ser Met
            35                  40                  45

Thr Leu Gly Ser Gly Ala Thr Phe Lys Ala Glu Trp Asn Ala Ala Val
        50                  55                  60

Asn Arg Gly Asn Phe Leu Ala Arg Arg Gly Leu Asp Phe Gly Ser Gln
 65                  70                  75                  80

Lys Lys Ala Thr Asp Tyr Ser Tyr Ile Gly Leu Asp Tyr Thr Val Thr
                 85                  90                  95
```

-continued

Tyr Arg Gln Thr Ala Ser Ala Ser Gly Asn Ser Arg Leu Cys Val Tyr
            100                 105                 110

Gly Trp Phe Gln Asn Arg Gly Val Gln Gly Val Pro Leu Val Glu Tyr
            115                 120                 125

Tyr Ile Ile Glu Asp Trp Val Asp Trp Val Pro Asp Ala Gln Gly Lys
            130                 135                 140

Met Val Thr Ile Asp Gly Ala Gln Tyr Lys Ile Phe Gln Met Asp His
145                 150                 155                 160

Thr Gly Pro Thr Ile Asn Gly Gly Ser Glu Thr Phe Lys Gln Tyr Phe
                165                 170                 175

Ser Val Arg Gln Gln Lys Arg Thr Ser Gly His Ile Thr Val Ser Asp
                180                 185                 190

His Phe Lys Glu Trp Ala Lys Gln Gly Trp Gly Ile Gly Asn Leu Tyr
                195                 200                 205

Glu Val Ala Leu Asn Ala Glu Gly Trp Gln Ser Ser Gly Ile Ala Asp
            210                 215                 220

Val Thr Lys Leu Asp Val Tyr Thr Thr Gln Lys Gly Ser Asn Pro Thr
225                 230                 235                 240

Thr Ala Ala Arg Thr Thr Arg Thr Thr Ala Arg Thr Ala Arg Thr
                245                 250                 255

Thr Thr Arg Thr Lys Thr Leu Pro Thr Asn Asn Lys Cys Ser Ser Lys
                260                 265                 270

Ile Thr Ala Gln Gly Tyr Lys Cys Cys Ser Asn Pro Asn Cys Glu Ile
            275                 280                 285

Val Tyr Ser Asp Asp Gly Thr Trp Gly Val Glu Asn Asn Glu Trp
290                 295                 300

Cys Gly Cys Gly Leu Glu Lys Cys Ser Ser Lys Ile Thr Ala Gln Gly
305                 310                 315                 320

Tyr Lys Cys Cys Ser Asp Pro Asn Cys Val Val Tyr Tyr Thr Asp Asp
                325                 330                 335

Asp Gly Lys Trp Gly
            340

<210> SEQ ID NO 21
<211> LENGTH: 341
<212> TYPE: PRT
<213> ORGANISM: Neocallimastix frontalis

<400> SEQUENCE: 21

Thr Val Ala Lys Ala Gln Trp Gly Gly Ala Ser Ala Gly Gln Lys
1               5                   10                  15

Leu Ser Val Gly Gly Gln Asn Gln His Lys Gly Val Ser Asp Gly
            20                  25                  30

Phe Ser Tyr Glu Ile Trp Leu Asp Asn Thr Gly Gly Ser Gly Ser Met
            35                  40                  45

Thr Leu Gly Ser Gly Ala Thr Phe Lys Ala Glu Trp Asn Ala Ala Val
50                  55                  60

Asn Arg Gly Asn Phe Leu Ala Arg Arg Gly Leu Asp Phe Gly Ser Gln
65                  70                  75                  80

Lys Lys Ala Thr Asp Tyr Ser Tyr Ile Gly Leu Asp Tyr Thr Ala Thr
                85                  90                  95

Tyr Arg Gln Thr Ala Ser Ala Ser Gly Asn Ser Arg Leu Cys Val Tyr
            100                 105                 110

Gly Trp Phe Gln Asn Arg Gly Val Gln Gly Val Pro Leu Val Glu Tyr

```
            115                 120                 125
Tyr Ile Ile Glu Asp Trp Val Asp Trp Val Pro Asp Ala Gln Gly Lys
130                 135                 140

Met Val Thr Ile Asp Gly Ala Gln Tyr Lys Ile Phe Gln Met Asp His
145                 150                 155                 160

Thr Gly Pro Thr Ile Asn Gly Gly Ser Glu Thr Phe Lys Gln Tyr Phe
                165                 170                 175

Ser Val Arg Gln Gln Lys Arg Thr Ser Gly His Ile Thr Val Ser Asp
                180                 185                 190

His Phe Lys Glu Trp Ala Lys Gln Gly Trp Gly Ile Gly Asn Leu Tyr
                195                 200                 205

Glu Val Ala Leu Asn Ala Glu Gly Trp Gln Ser Ser Gly Ile Ala Asp
210                 215                 220

Val Thr Lys Leu Asp Val Tyr Thr Thr Gln Lys Gly Ser Asn Pro Thr
225                 230                 235                 240

Thr Ala Ala Arg Thr Thr Arg Thr Thr Ala Arg Thr Thr Ala Arg Thr
                245                 250                 255

Thr Thr Arg Thr Lys Thr Leu Pro Thr Asn Asn Lys Cys Ser Ser Lys
                260                 265                 270

Ile Thr Ala Gln Gly Tyr Lys Cys Ser Ser Asn Pro Asn Cys Glu Ile
                275                 280                 285

Val Tyr Thr Asp Asp Gly Thr Trp Gly Val Glu Asn Asn Glu Trp
290                 295                 300

Cys Gly Cys Gly Leu Glu Lys Cys Ser Ser Lys Ile Thr Ala Gln Gly
305                 310                 315                 320

Tyr Lys Cys Arg Ser Asp Pro Asn Cys Val Val Tyr Tyr Thr Asp Asp
                325                 330                 335

Asp Gly Lys Trp Gly
                340

<210> SEQ ID NO 22
<211> LENGTH: 341
<212> TYPE: PRT
<213> ORGANISM: Neocallimastix patriciarum

<400> SEQUENCE: 22

Thr Val Ala Lys Ala Gln Trp Gly Gly Gly Ala Ser Ala Gly Gln Lys
1               5                   10                  15

Leu Ser Val Gly Gly Gly Gln Asn Gln His Lys Gly Val Ser Asp Gly
                20                  25                  30

Phe Ser Tyr Glu Ile Trp Leu Asp Asn Thr Gly Gly Ser Gly Ser Met
            35                  40                  45

Thr Leu Gly Ser Gly Ala Thr Phe Lys Ala Glu Trp Asn Ala Ala Val
    50                  55                  60

Asn Arg Gly Asn Phe Leu Ala Arg Arg Gly Leu Asp Phe Gly Ser Gln
65                  70                  75                  80

Lys Lys Ala Thr Asp Tyr Ser Tyr Ile Gly Leu Asp Tyr Thr Ala Thr
                85                  90                  95

Tyr Arg Gln Thr Ala Ser Ala Ser Gly Asn Ser Arg Leu Cys Val Tyr
                100                 105                 110

Gly Trp Phe Gln Asn Arg Gly Val Gln Gly Val Pro Leu Val Glu Tyr
            115                 120                 125

Tyr Ile Ile Glu Asp Trp Val Asp Trp Val Pro Asp Ala Gln Gly Lys
130                 135                 140
```

```
Met Val Thr Ile Asp Gly Ala Gln Tyr Lys Ile Phe Gln Met Asp His
145                 150                 155                 160

Thr Gly Pro Thr Ile Asn Gly Gly Ser Glu Thr Phe Lys Gln Tyr Phe
                165                 170                 175

Ser Val Arg Gln Gln Lys Arg Thr Ser Gly His Ile Thr Val Ser Asp
            180                 185                 190

His Phe Lys Glu Trp Ala Lys Gln Gly Trp Gly Ile Gly Asn Leu Tyr
        195                 200                 205

Glu Val Ala Leu Asn Ala Glu Gly Trp Gln Ser Ser Gly Ile Ala Asp
    210                 215                 220

Val Thr Lys Leu Asp Val Tyr Thr Thr Gln Lys Gly Ser Asn Pro Thr
225                 230                 235                 240

Thr Ala Ala Arg Thr Thr Arg Thr Thr Ala Arg Thr Thr Ala Arg Thr
                245                 250                 255

Thr Thr Arg Thr Lys Thr Leu Pro Thr Asn Asn Lys Cys Ser Ser Lys
                260                 265                 270

Ile Thr Ala Gln Gly Tyr Lys Cys Cys Ser Asn Pro Asn Cys Glu Ile
            275                 280                 285

Val Tyr Thr Asp Asp Gly Thr Trp Gly Val Glu Asn Asn Glu Trp
    290                 295                 300

Cys Gly Cys Gly Leu Glu Glu Cys Ser Ser Lys Ile Thr Ala Gln Gly
305                 310                 315                 320

Tyr Lys Cys Arg Ser Asp Pro Asn Cys Val Val Tyr Thr Asp Asp
                325                 330                 335

Asp Gly Lys Trp Gly
            340

<210> SEQ ID NO 23
<211> LENGTH: 341
<212> TYPE: PRT
<213> ORGANISM: Neocallimastix patriciarum

<400> SEQUENCE: 23

Thr Val Ala Lys Ala Gln Trp Gly Gly Gly Ala Ser Ala Gly Gln Lys
1               5                   10                  15

Leu Ser Val Gly Gly Gly Gln Asn Gln His Lys Gly Val Ser Asp Gly
            20                  25                  30

Phe Ser Tyr Glu Ile Trp Ser Asp Asn Thr Gly Gly Ser Gly Ser Met
        35                  40                  45

Thr Leu Gly Ser Gly Ala Thr Phe Lys Ala Glu Trp Asn Ala Ala Val
    50                  55                  60

Asn Arg Gly Asn Phe Leu Ala Arg Arg Gly Leu Asp Phe Gly Ser Gln
65                  70                  75                  80

Lys Lys Ala Thr Asp Tyr Ser Tyr Ile Gly Leu Asp Tyr Thr Ala Thr
                85                  90                  95

Tyr Arg Gln Thr Ala Ser Ala Ser Gly Asn Ser Arg Leu Cys Val Tyr
            100                 105                 110

Gly Trp Phe Gln Asn Arg Gly Val Gln Gly Val Pro Leu Val Glu Tyr
        115                 120                 125

Tyr Ile Ile Glu Asp Trp Val Asp Trp Val Pro Asp Ala Gln Gly Lys
    130                 135                 140

Met Val Thr Ile Asp Gly Ala Gln Tyr Lys Ile Phe Gln Met Asp His
145                 150                 155                 160

Thr Gly Pro Thr Ile Asn Gly Gly Ser Glu Thr Phe Lys Gln Tyr Phe
                165                 170                 175
```

Ser Val Arg Gln Gln Lys Arg Thr Ser Gly His Ile Thr Val Ser Asp
            180                 185                 190

His Phe Lys Glu Trp Ala Lys Gln Gly Trp Gly Ile Gly Asn Leu Tyr
            195                 200                 205

Glu Val Ala Leu Asn Ala Glu Gly Trp Gln Ser Ser Gly Ile Ala Asp
            210                 215                 220

Val Thr Lys Leu Asp Val Tyr Thr Thr Gln Lys Gly Ser Asn Pro Thr
225                 230                 235                 240

Thr Ala Ala Arg Thr Thr Arg Thr Thr Ala Arg Thr Thr Ala Arg Thr
            245                 250                 255

Thr Thr Arg Thr Lys Thr Leu Pro Thr Asn Asn Lys Cys Ser Ser Lys
            260                 265                 270

Ile Thr Ala Gln Gly Tyr Lys Cys Cys Ser Asn Pro Asn Cys Glu Ile
            275                 280                 285

Val Tyr Thr Asp Asp Asp Gly Thr Trp Gly Val Glu Asn Asn Glu Trp
            290                 295                 300

Cys Gly Cys Gly Leu Glu Lys Cys Ser Ser Lys Ile Thr Ala Gln Gly
305                 310                 315                 320

Tyr Lys Cys Cys Ser Asp Pro Asn Cys Val Val Tyr Thr Asp Asp
            325                 330                 335

Asp Gly Lys Trp Gly
            340

<210> SEQ ID NO 24
<211> LENGTH: 341
<212> TYPE: PRT
<213> ORGANISM: Neocallimastix patriciarum

<400> SEQUENCE: 24

Thr Val Ala Lys Ala Gln Trp Gly Gly Gly Ala Ser Ala Gly Gln Lys
1               5                   10                  15

Leu Ser Val Gly Gly Gln Asn Gln His Lys Gly Val Ser Asp Gly
            20                  25                  30

Phe Ser Tyr Glu Ile Trp Leu Asp Asn Thr Gly Gly Ser Gly Ser Met
            35                  40                  45

Ile Leu Gly Ser Gly Ala Thr Phe Lys Ala Glu Trp Asn Ala Ala Val
50                  55                  60

Asn Arg Gly Asn Phe Leu Ala Arg Arg Gly Leu Asp Phe Gly Ser Gln
65                  70                  75                  80

Lys Lys Ala Thr Asp Tyr Ser Tyr Ile Gly Leu Asp Tyr Thr Ala Thr
            85                  90                  95

Tyr Arg Gln Thr Ala Ser Ala Ser Gly Asn Ser Arg Leu Cys Val Tyr
            100                 105                 110

Gly Trp Phe Gln Asn Arg Gly Val Gln Gly Val Pro Leu Val Glu Tyr
            115                 120                 125

Tyr Ile Ile Glu Asp Trp Val Asp Trp Val Pro Asp Ala Gln Gly Lys
            130                 135                 140

Met Val Thr Ile Asp Gly Ala Gln Tyr Lys Ile Phe Gln Met Asp His
145                 150                 155                 160

Thr Gly Pro Thr Ile Asn Gly Gly Ser Glu Thr Phe Lys Gln Tyr Phe
            165                 170                 175

Ser Val Arg Gln Gln Lys Arg Thr Ser Gly His Ile Thr Val Ser Asp
            180                 185                 190

His Phe Lys Glu Trp Ala Lys His Gly Trp Gly Ile Gly Asn Leu Tyr

```
            195                 200                 205
Glu Val Ala Leu Asn Ala Glu Gly Trp Gln Ser Ser Gly Ile Ala Asp
    210                 215                 220

Val Thr Lys Leu Asp Val Tyr Thr Thr Gln Lys Gly Ser Asn Pro Thr
225                 230                 235                 240

Thr Ala Ala Arg Thr Thr Arg Thr Thr Ala Arg Thr Thr Ala Arg Thr
                245                 250                 255

Thr Thr Arg Thr Lys Thr Leu Pro Thr Asn Asn Lys Cys Ser Ser Lys
            260                 265                 270

Ile Thr Ala Gln Gly Tyr Lys Cys Cys Ser Asn Pro Asn Cys Glu Ile
            275                 280                 285

Val Tyr Thr Asp Asp Gly Thr Trp Gly Val Glu Asn Asn Glu Trp
    290                 295                 300

Cys Gly Cys Gly Leu Glu Lys Cys Ser Ser Lys Ile Thr Ala Gln Gly
305                 310                 315                 320

Tyr Lys Cys Cys Ser Asp Pro Asn Cys Val Val Tyr Tyr Thr Asp Asp
                325                 330                 335

Asp Gly Lys Trp Gly
            340

<210> SEQ ID NO 25
<211> LENGTH: 337
<212> TYPE: PRT
<213> ORGANISM: Neocallimastix frontalis

<400> SEQUENCE: 25

Thr Val Ala Lys Ala Gln Trp Gly Gly Gly Ser Ala Gly Gln Lys
1               5                   10                  15

Leu Ser Val Gly Gly Gln Asn Gln His Lys Gly Val Ser Asp Gly
            20                  25                  30

Phe Ser Tyr Glu Ile Trp Leu Asp Asn Thr Gly Gly Ser Gly Ser Met
                35                  40                  45

Thr Leu Gly Ser Gly Ala Thr Phe Lys Ala Glu Trp Asn Ala Ala Val
    50                  55                  60

Asn Arg Gly Asn Phe Leu Ala Arg Arg Gly Leu Asp Phe Gly Ser Gln
65                  70                  75                  80

Lys Lys Ala Ala Asp Tyr Ser Tyr Ile Gly Leu Asp Tyr Thr Ala Thr
                85                  90                  95

Tyr Arg Gln Thr Ala Ser Ala Ser Gly Asn Ser Arg Leu Cys Val Tyr
                100                 105                 110

Gly Trp Phe Gln Asn Arg Gly Val Gln Gly Val Pro Leu Val Glu Tyr
            115                 120                 125

Tyr Ile Ile Glu Asp Trp Val Asp Trp Val Pro Asp Ala Gln Gly Lys
    130                 135                 140

Met Val Thr Ile Asp Gly Ala Gln Tyr Lys Ile Phe Gln Met Asp His
145                 150                 155                 160

Thr Gly Pro Thr Ile Asn Gly Gly Ser Glu Thr Phe Lys Gln Tyr Phe
                165                 170                 175

Ser Val Arg Gln Gln Lys Arg Thr Ser Gly His Ile Thr Val Ser Asp
            180                 185                 190

His Phe Lys Glu Trp Ala Lys Gln Gly Trp Gly Ile Gly Asn Leu Tyr
            195                 200                 205

Glu Val Ala Leu Asn Ala Glu Gly Trp Gln Ser Ser Gly Val Ala Asp
    210                 215                 220
```

```
Val Thr Leu Leu Asp Val Tyr Thr Thr Pro Lys Gly Ser Ser Pro Ala
225                 230                 235                 240

Thr Ser Ala Ala Pro Arg Thr Thr Thr Arg Thr Thr Thr Arg Thr Lys
                245                 250                 255

Ser Leu Pro Thr Asn Tyr Asn Lys Cys Ser Ala Arg Ile Thr Ala Gln
                260                 265                 270

Gly Tyr Lys Cys Cys Ser Asp Pro Asn Cys Val Val Tyr Tyr Thr Asp
            275                 280                 285

Asp Asp Gly Thr Trp Gly Val Glu Asn Asn Glu Trp Cys Gly Cys Gly
        290                 295                 300

Val Glu Gln Cys Ser Ser Lys Ile Thr Ser Gln Gly Tyr Lys Cys Cys
305                 310                 315                 320

Ser Asp Pro Asn Cys Val Val Phe Tyr Thr Asp Asp Gly Lys Trp
                325                 330                 335

Gly

<210> SEQ ID NO 26
<211> LENGTH: 337
<212> TYPE: PRT
<213> ORGANISM: Neocallimastix frontalis

<400> SEQUENCE: 26

Thr Val Ala Lys Ala Gln Trp Gly Gly Gly Ala Ser Ala Gly Gln Lys
1               5                   10                  15

Leu Ser Val Gly Gly Gly Gln Asn Gln His Lys Gly Val Ser Asp Gly
            20                  25                  30

Phe Ser Tyr Glu Ile Trp Leu Asp Asn Thr Gly Gly Ser Gly Ser Met
        35                  40                  45

Thr Leu Gly Ser Gly Ala Thr Phe Lys Ala Glu Trp Asn Ala Ala Val
    50                  55                  60

Asn Arg Gly Asn Phe Leu Ala Arg Arg Gly Leu Asp Phe Gly Ser Gln
65                  70                  75                  80

Lys Lys Ala Thr Asp Tyr Ser Tyr Ile Gly Leu Asp Tyr Thr Ala Thr
                85                  90                  95

Tyr Arg Gln Thr Ala Ser Ala Ser Gly Asn Ser Arg Leu Cys Val Tyr
            100                 105                 110

Gly Trp Phe Gln Asn Arg Gly Val Gln Gly Val Pro Leu Val Glu Tyr
        115                 120                 125

Tyr Ile Ile Glu Asp Trp Val Asp Trp Val Pro Asp Ala Gln Gly Lys
    130                 135                 140

Met Val Thr Ile Asp Gly Ala Gln Tyr Lys Ile Phe Gln Met Asp His
145                 150                 155                 160

Thr Gly Pro Thr Ile Asn Gly Gly Ser Glu Thr Phe Lys Gln Tyr Phe
                165                 170                 175

Ser Val Arg Gln Gln Lys Arg Thr Ser Gly His Ile Thr Val Ser Asp
            180                 185                 190

His Phe Lys Glu Trp Ala Lys Gln Gly Trp Gly Ile Gly Asn Leu Tyr
        195                 200                 205

Glu Val Ala Leu Asn Ala Glu Gly Trp Gln Ser Ser Gly Val Ala Asp
    210                 215                 220

Val Thr Leu Leu Asp Val Tyr Thr Thr Pro Lys Gly Ser Ser Pro Ala
225                 230                 235                 240

Thr Ser Ala Ala Pro Arg Thr Thr Thr Arg Thr Thr Thr Arg Thr Lys
                245                 250                 255
```

```
Ser Leu Pro Thr Asn Tyr Asn Lys Cys Ser Ala Arg Ile Thr Ala Gln
            260                 265                 270

Gly Tyr Lys Cys Cys Ser Asp Pro Asn Cys Val Val Tyr Tyr Thr Asp
            275                 280                 285

Asp Asp Gly Thr Trp Val Glu Asn Glu Trp Arg Gly Cys Gly
        290                 295                 300

Val Glu Gln Cys Ser Ser Lys Ile Thr Ser Gln Gly Tyr Lys Cys Cys
305                 310                 315                 320

Ser Asp Pro Asn Cys Val Val Phe Tyr Thr Asp Asp Gly Lys Trp
            325                 330                 335

Gly

<210> SEQ ID NO 27
<211> LENGTH: 337
<212> TYPE: PRT
<213> ORGANISM: Neocallimastix patriciarum

<400> SEQUENCE: 27

Thr Val Ala Lys Ala Gln Trp Gly Gly Gly Ala Ser Ala Gly Gln Lys
1               5                   10                  15

Leu Ser Val Gly Gly Gln Asn Gln His Lys Gly Val Ser Asp Gly
            20                  25                  30

Phe Ser Tyr Glu Ile Trp Leu Asp Asn Thr Gly Ser Gly Ser Met
            35                  40                  45

Thr Leu Gly Ser Gly Ala Thr Phe Lys Ala Glu Trp Asn Ala Ala Val
    50                  55                  60

Asn Arg Gly Asn Phe Leu Ala Arg Arg Gly Leu Asp Phe Gly Ser Gln
65                  70                  75                  80

Lys Lys Ala Thr Asp Tyr Ser Tyr Ile Gly Leu Asp Tyr Thr Ala Thr
            85                  90                  95

Tyr Arg Gln Thr Ala Ser Ala Ser Gly Asn Ser Arg Leu Cys Val Tyr
            100                 105                 110

Gly Trp Phe Gln Asn Arg Gly Val Gln Gly Val Pro Leu Val Glu Tyr
            115                 120                 125

Tyr Ile Ile Glu Asp Trp Val Asp Trp Val Pro Asp Ala Gln Gly Lys
            130                 135                 140

Met Val Thr Ile Asp Gly Ala Gln Tyr Lys Ile Phe Gln Met Asp His
145                 150                 155                 160

Thr Gly Pro Thr Ile Asn Gly Gly Ser Glu Thr Phe Lys Gln Tyr Phe
            165                 170                 175

Ser Val Arg Gln Gln Lys Arg Thr Ser Gly His Ile Thr Val Ser Asp
            180                 185                 190

His Phe Lys Glu Trp Ala Lys Gln Gly Trp Gly Ile Gly Asn Leu Tyr
            195                 200                 205

Glu Val Ala Leu Asn Ala Glu Gly Trp Gln Ser Ser Gly Val Ala Asp
            210                 215                 220

Val Thr Leu Leu Asp Val Tyr Thr Thr Pro Lys Gly Ser Ser Pro Ala
225                 230                 235                 240

Thr Ser Ala Ala Pro Arg Thr Thr Thr Arg Thr Thr Arg Thr Lys
            245                 250                 255

Ser Leu Pro Thr Asn Tyr Asn Lys Cys Ser Ala Arg Ile Thr Ala Gln
            260                 265                 270

Gly Tyr Lys Cys Cys Ser Asp Pro Asn Cys Val Val Tyr Tyr Thr Asp
            275                 280                 285
```

```
Asp Asp Gly Thr Trp Gly Val Glu Asn Asn Glu Trp Cys Gly Cys Gly
    290                 295                 300

Val Glu Gln Cys Ser Ser Lys Ile Thr Ser Gln Gly Tyr Lys Cys Cys
305                 310                 315                 320

Ser Asp Pro Asn Cys Val Val Phe Tyr Thr Asp Asp Gly Lys Trp
                325                 330                 335

Gly

<210> SEQ ID NO 28
<211> LENGTH: 969
<212> TYPE: DNA
<213> ORGANISM: Neocallimastix patriciarum

<400> SEQUENCE: 28
gctccagctc ttgcccaatg gggcggcgga tgggacttcg gcggtttcgg aggaggcttc      60
ggaggaggct tcggtggtaa taacaacggt ggagctgtta ctggtaatac taatggtggt     120
attgatgatc aatctggaga atctatccgt attatgccaa tgggtgattc tatcacattt     180
ggtattggtg aaactggtgg ttacagaaag tacctttaca gcgatttaac caaacaaggt     240
tacaaaattg atatggttgg tccagaagga tcaagtcgtg ctaccgaaaa tggtattaca     300
tttgatgaca tcacgctgg ttacagtgga tacaccatca aaaacggtct cgaattcttc      360
agaggtcttg aaggaaatgg aagtttatat gatgtcctta aattgaaaca ttctgttaaa     420
ttagctaaac cagatatcat tcttcttatc attggtacca atgatatgtc cggaaatcac     480
tctacccaat cttgtactaa tgatcttcat gatcttttag attatgttat tggtgaaatg     540
ccatctcatt gtactatctt cctttcttct attccagatt tacaaactaa caacgcccaa     600
aatgttcttt cttacaacga agcagttaag aaggttgtta gcgaatacca aggaaagggt     660
aagaatgtta gatttgctga tattcacggt tgtatgaacg gtatggctga tatgagttct     720
gataaggttc atccaagtgg atctggttac aagaagatgg tgactactt tgctacagtt      780 gttgacagct ttattaagga aaatccagac ttcagaggta ccagttcctc taacaaggcc     840
actaccacca aggccactac cccaaccacc ggtaatacca cttgttccgc taagattact     900
agccaaggct acaagtgttg ttctgctagc tgtgttgttg tctacactga caacgacgga     960
gattgggggg                                                            969

<210> SEQ ID NO 29
<211> LENGTH: 957
<212> TYPE: DNA
<213> ORGANISM: Neocallimastix frontalis

<400> SEQUENCE: 29
actgttgcta aggcccaatg gggtggtttt ggtgacttcg gaggcttcgg aggctttggt      60
ggcttcggtg ataacggtaa taatggcaat aataataaca atggtggtaa tgttgctgta     120
tcaggtgata ctgttaaaat tatgcctgtt ggtgattcta tcacttttgg tgaaggtgaa     180
agaggtggat acagaaagta tctttacagt gccttaactc aaaaaggtta taaaattgat     240
atggtaggtc cagagggatc caacagtgct tcagctaatg gtattcaata tgatgataat     300
aatgctggtt acagtggatt ccaaattaaa gaaattccag ttggggtca acaacaaggt      360 ggtgaaggca gtttatacaa taaacttaag agtaagaatg ctgttaagca atctcaacca     420
gatatcattc ttcttatcat tggtactaat gatatgaccg ccaatcgttc aatggatgct     480
tgtgccaatg atcttcgtgc tctttttagat tatatgcttg gagatatgcc agccaatagt     540
```

```
attatcttta tgggttctat tccagaattt actgcctacg gtggtaattc tcaaagaatt     600
gctaattaca atggtacagt taagaaggtt gctgatgaat acgctaataa gggtaagaat     660
gttagatttg ctgatgttca tggttgtctt aacggtatgg ctgatattgg tggtgaccaa     720
cttcacccaa gtggaaatgg ttataaaaaa attggtaact tctgggctgg agttgtcgat     780
gaataccttc aatctatcaa atctaataac ggtggtaagg aagatgaaac cggtagtggt     840
agtggcaatg gtgaagtaga acttagtaat tgttcaagta aaattactag acaaggttac     900
aaatgttgtt ctaagaattg tgtagtcatc tacactgatg ccgatggtaa atgggt         957
```

<210> SEQ ID NO 30
<211> LENGTH: 957
<212> TYPE: DNA
<213> ORGANISM: Neocallimastix patriciarum

<400> SEQUENCE: 30

```
actgttgcta aggcccaatg gggtggtttt ggtgacttcg gaggcttcgg aggctttggt      60
ggcttcggtg ataacggtaa taatggcaat aataataaca atggtggtaa tgttgctgta     120
tcaggtgata ctgttaaaat tatgcctgtt ggtgattcta tcacttttgg tgaaggtgaa     180
agaggtggat acagaaagta tctttacagt gccttaactc aaaaaggtta taaaattgat     240
atggtaggtc cagagggatc caacagtgct tcagctaatg gtattcaata tgatgataat     300
aatgctggtt acagtggatt ccaaattaaa gaaattccag gttggggtca acaacaaggt     360
ggtgaaggca gtttatacaa taaacttaag agtaagaatg ctgttaagca atctcaacca     420
gatatcattc ttcttatcat tggtactaat gatatgaccg ccaatcgttc aatggatgct     480
tgtgccaatg atcttcgtgc tcttttagat tatatgcttg gagatatgcc agccaatagt     540
attatcttta tgggttctat tccagaattt actgcctacg gtggtaattc tcaaagaatt     600
gctaattaca atggtacagt taagaaggtt gctgatgaat acgctaataa gggtaagaat     660
gttagatttg ctgatgttca tggttgtctt aacggtatgg ctgatattgg tggtgaccaa     720
cttcacccaa gtggaaatgg ttataaaaaa attggtaact tctgggctgg agttgtcgat     780
gaataccttc aatctatcaa atctaataac ggtggtaagg aagatgaaac cggtagtggt     840
agtggcaatg gtgaagtaga acttagtaat tgttcaagta aaattactag acaaggttac     900
aaatgttgtt ctaagaattg tgtagtcatc tacactgatg acgatggtaa atgggt         957
```

<210> SEQ ID NO 31
<211> LENGTH: 323
<212> TYPE: PRT
<213> ORGANISM: Neocallimastix patriciarum

<400> SEQUENCE: 31

```
Ala Pro Ala Leu Ala Gln Trp Gly Gly Gly Trp Asp Phe Gly Gly Phe
1               5                   10                  15

Gly Gly Gly Phe Gly Gly Phe Gly Asn Asn Asn Gly Gly Ala
            20                  25                  30

Val Thr Gly Asn Thr Asn Gly Gly Ile Asp Asp Gln Ser Gly Glu Ser
        35                  40                  45

Ile Arg Ile Met Pro Met Gly Asp Ser Ile Thr Phe Gly Ile Gly Glu
    50                  55                  60

Thr Gly Gly Tyr Arg Lys Tyr Leu Tyr Ser Asp Leu Thr Lys Gln Gly
65                  70                  75                  80

Tyr Lys Ile Asp Met Val Gly Pro Glu Gly Ser Ser Arg Ala Thr Glu
                85                  90                  95
```

```
Asn Gly Ile Thr Phe Asp Asp Asn His Ala Gly Tyr Ser Gly Tyr Thr
            100                 105                 110

Ile Lys Asn Gly Leu Glu Phe Phe Arg Gly Leu Glu Gly Asn Gly Ser
            115                 120                 125

Leu Tyr Asp Val Leu Lys Leu Lys His Ser Val Lys Leu Ala Lys Pro
            130                 135                 140

Asp Ile Ile Leu Leu Ile Ile Gly Thr Asn Asp Met Ser Gly Asn His
145                 150                 155                 160

Ser Thr Gln Ser Cys Thr Asn Asp Leu His Asp Leu Leu Asp Tyr Val
                165                 170                 175

Ile Gly Glu Met Pro Ser His Cys Thr Ile Phe Leu Ser Ser Ile Pro
            180                 185                 190

Asp Leu Gln Thr Asn Asn Ala Gln Asn Val Leu Ser Tyr Asn Glu Ala
            195                 200                 205

Val Lys Lys Val Val Ser Glu Tyr Gln Gly Lys Gly Lys Asn Val Arg
210                 215                 220

Phe Ala Asp Ile His Gly Cys Met Asn Gly Met Ala Asp Met Ser Ser
225                 230                 235                 240

Asp Lys Val His Pro Ser Gly Ser Gly Tyr Lys Lys Met Gly Asp Tyr
                245                 250                 255

Phe Ala Thr Val Val Asp Ser Phe Ile Lys Glu Asn Pro Asp Phe Arg
            260                 265                 270

Gly Thr Ser Ser Ser Asn Lys Ala Thr Thr Thr Lys Ala Thr Thr Pro
            275                 280                 285

Thr Thr Gly Asn Thr Thr Cys Ser Ala Lys Ile Thr Ser Gln Gly Tyr
            290                 295                 300

Lys Cys Cys Ser Ala Ser Cys Val Val Val Tyr Thr Asp Asn Asp Gly
305                 310                 315                 320

Asp Trp Gly

<210> SEQ ID NO 32
<211> LENGTH: 319
<212> TYPE: PRT
<213> ORGANISM: Neocallimastix frontalis

<400> SEQUENCE: 32

Thr Val Ala Lys Ala Gln Trp Gly Gly Phe Gly Asp Phe Gly Gly Phe
1               5                   10                  15

Gly Gly Phe Gly Gly Phe Gly Asp Asn Gly Asn Asn Gly Asn Asn Asn
            20                  25                  30

Asn Asn Gly Gly Asn Val Ala Val Ser Gly Asp Thr Val Lys Ile Met
            35                  40                  45

Pro Val Gly Asp Ser Ile Thr Phe Gly Glu Gly Glu Arg Gly Gly Tyr
50                  55                  60

Arg Lys Tyr Leu Tyr Ser Ala Leu Thr Gln Lys Gly Tyr Lys Ile Asp
65                  70                  75                  80

Met Val Gly Pro Glu Gly Ser Asn Ser Ala Ser Ala Asn Gly Ile Gln
                85                  90                  95

Tyr Asp Asp Asn Asn Ala Gly Tyr Ser Gly Phe Gln Ile Lys Glu Ile
            100                 105                 110

Pro Gly Trp Gly Gln Gln Gln Gly Gly Glu Gly Ser Leu Tyr Asn Lys
            115                 120                 125

Leu Lys Ser Lys Asn Ala Val Lys Gln Ser Gln Pro Asp Ile Ile Leu
            130                 135                 140
```

-continued

```
Leu Ile Ile Gly Thr Asn Asp Met Thr Ala Asn Arg Ser Met Asp Ala
145                 150                 155                 160

Cys Ala Asn Asp Leu Arg Ala Leu Leu Asp Tyr Met Leu Gly Asp Met
                165                 170                 175

Pro Ala Asn Ser Ile Ile Phe Met Gly Ser Ile Pro Glu Phe Thr Ala
            180                 185                 190

Tyr Gly Gly Asn Ser Gln Arg Ile Ala Asn Tyr Asn Gly Thr Val Lys
        195                 200                 205

Lys Val Ala Asp Glu Tyr Ala Asn Lys Gly Lys Asn Val Arg Phe Ala
    210                 215                 220

Asp Val His Gly Cys Leu Asn Gly Met Ala Asp Ile Gly Gly Asp Gln
225                 230                 235                 240

Leu His Pro Ser Gly Asn Gly Tyr Lys Lys Ile Gly Asn Phe Trp Ala
                245                 250                 255

Gly Val Val Asp Glu Tyr Leu Gln Ser Ile Lys Ser Asn Asn Gly Gly
            260                 265                 270

Lys Glu Asp Glu Thr Gly Ser Gly Ser Gly Asn Gly Glu Val Glu Leu
        275                 280                 285

Ser Asn Cys Ser Ser Lys Ile Thr Arg Gln Gly Tyr Lys Cys Cys Ser
    290                 295                 300

Lys Asn Cys Val Val Ile Tyr Thr Asp Ala Asp Gly Lys Trp Gly
305                 310                 315

<210> SEQ ID NO 33
<211> LENGTH: 319
<212> TYPE: PRT
<213> ORGANISM: Neocallimastix patriciarum

<400> SEQUENCE: 33

Thr Val Ala Lys Ala Gln Trp Gly Gly Phe Gly Asp Phe Gly Gly Phe
1               5                  10                  15

Gly Gly Phe Gly Gly Phe Gly Asp Asn Gly Asn Asn Gly Asn Asn Asn
            20                  25                  30

Asn Asn Gly Gly Asn Val Ala Val Ser Gly Asp Thr Val Lys Ile Met
        35                  40                  45

Pro Val Gly Asp Ser Ile Thr Phe Gly Glu Gly Glu Arg Gly Gly Tyr
    50                  55                  60

Arg Lys Tyr Leu Tyr Ser Ala Leu Thr Gln Lys Gly Tyr Lys Ile Asp
65                  70                  75                  80

Met Val Gly Pro Glu Gly Ser Asn Ser Ala Ser Ala Asn Gly Ile Gln
                85                  90                  95

Tyr Asp Asp Asn Asn Ala Gly Tyr Ser Gly Phe Gln Ile Lys Glu Ile
            100                 105                 110

Pro Gly Trp Gly Gln Gln Gln Gly Gly Glu Gly Ser Leu Tyr Asn Lys
        115                 120                 125

Leu Lys Ser Lys Asn Ala Val Lys Gln Ser Gln Pro Asp Ile Ile Leu
    130                 135                 140

Leu Ile Ile Gly Thr Asn Asp Met Thr Ala Asn Arg Ser Met Asp Ala
145                 150                 155                 160

Cys Ala Asn Asp Leu Arg Ala Leu Leu Asp Tyr Met Leu Gly Asp Met
                165                 170                 175

Pro Ala Asn Ser Ile Ile Phe Met Gly Ser Ile Pro Glu Phe Thr Ala
            180                 185                 190

Tyr Gly Gly Asn Ser Gln Arg Ile Ala Asn Tyr Asn Gly Thr Val Lys
```

-continued

```
            195                 200                 205
Lys Val Ala Asp Glu Tyr Ala Asn Lys Gly Lys Asn Val Arg Phe Ala
    210                 215                 220

Asp Val His Gly Cys Leu Asn Gly Met Ala Asp Ile Gly Gly Asp Gln
225                 230                 235                 240

Leu His Pro Ser Gly Asn Gly Tyr Lys Lys Ile Gly Asn Phe Trp Ala
            245                 250                 255

Gly Val Val Asp Glu Tyr Leu Gln Ser Ile Lys Ser Asn Asn Gly Gly
            260                 265                 270

Lys Glu Asp Glu Thr Gly Ser Gly Ser Gly Asn Gly Glu Val Glu Leu
            275                 280                 285

Ser Asn Cys Ser Ser Lys Ile Thr Arg Gln Gly Tyr Lys Cys Cys Ser
    290                 295                 300

Lys Asn Cys Val Val Ile Tyr Thr Asp Ala Asp Gly Lys Trp Gly
305                 310                 315
```